(12) United States Patent
Sterling et al.

(10) Patent No.: US 7,993,292 B2
(45) Date of Patent: Aug. 9, 2011

(54) ORTHOTIC APPARATUS AND METHOD OF OPERATION

(75) Inventors: Shane Sterling, Seattle, WA (US); Jay Bublitz, Shoreline, WA (US)

(73) Assignee: Bellacure, Inc., Seattle, WA (US)

( * ) Notice: Subject to any disclaimer, the term of this patent is extended or adjusted under 35 U.S.C. 154(b) by 451 days.

(21) Appl. No.: 12/150,183

(22) Filed: Apr. 25, 2008

(65) Prior Publication Data

US 2008/0294079 A1 Nov. 27, 2008

Related U.S. Application Data

(60) Provisional application No. 60/931,300, filed on May 22, 2007.

(51) Int. Cl.
*A61F 5/00* (2006.01)

(52) U.S. Cl. ............................. 602/13; 602/32

(58) Field of Classification Search .................... 602/13, 602/19, 32–35, 12; 128/882, DIG. 20
See application file for complete search history.

(56) References Cited

U.S. PATENT DOCUMENTS

| | | | | |
|---|---|---|---|---|
| 4,338,923 A * | 7/1982 | Gelfer et al. | .................. | 601/150 |
| 5,016,621 A * | 5/1991 | Bender | ........................... | 602/26 |
| 5,980,560 A | 11/1999 | Chang | | |
| 6,969,365 B2 * | 11/2005 | Scorvo | ............................. | 602/16 |
| 6,994,682 B2 | 2/2006 | Bauerfeind et al. | | |
| 7,150,721 B2 * | 12/2006 | Houser | ............................ | 602/16 |
| 2002/0052568 A1 * | 5/2002 | Houser et al. | ................... | 602/26 |

OTHER PUBLICATIONS

International Searching Authority, International Search Report, mailed on Nov. 17, 2008 for International Application No. PCT/US 08/06420 filed on May 19, 2008.
International Searching Authority, Written Opinion of the International Search Authority, mailed on Nov. 17, 2008 for International Application No. PCT/US 08/06420 filed on May 19, 2008.
Steven Ashley, "Artificial Muscles," Scientific American, pp. 53-59, (Oct. 2003).

* cited by examiner

*Primary Examiner* — Michael A. Brown
(74) *Attorney, Agent, or Firm* — Workman Nydegger

(57) ABSTRACT

Various embodiments of the invention relate to orthotic apparatuses configured to apply a controllable, therapeutic force to a subject. In one embodiment of the invention, an orthotic apparatus includes a frame structure and an actuator system operable to provide input energy of a first type (e.g., fluid pumped by a pump or an applied voltage). At least one strap structure is attached to the frame structure and operably coupled to the actuator system. The at least one strap structure may be configured to convert at least a portion of the input energy to energy of a second type, the energy of the second type being strain energy. Additional embodiments are directed to inflatable structures and methods of operating the orthotic apparatuses and inflatable structures disclosed herein.

22 Claims, 19 Drawing Sheets

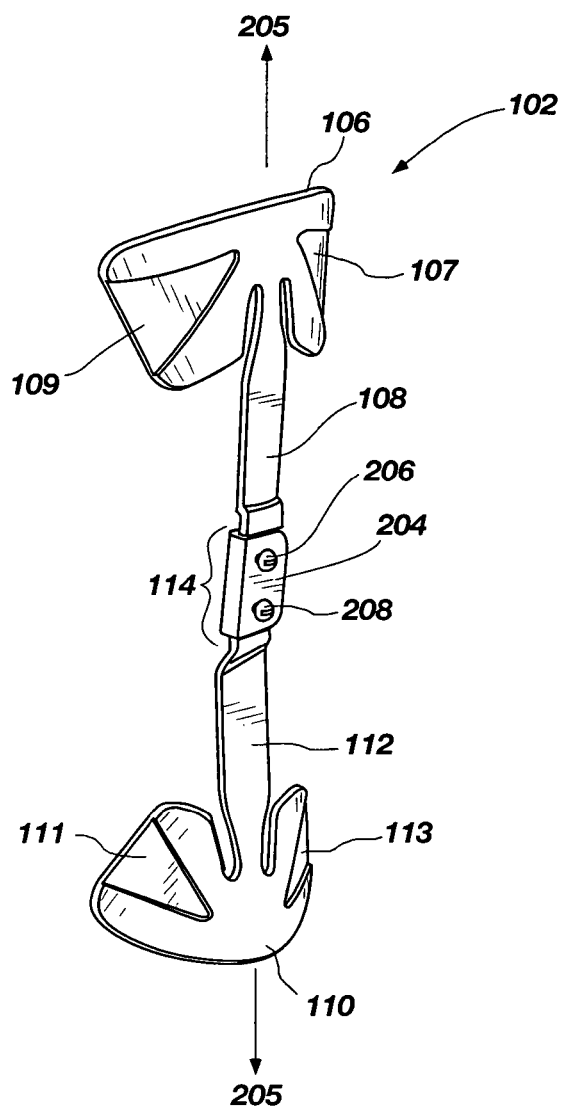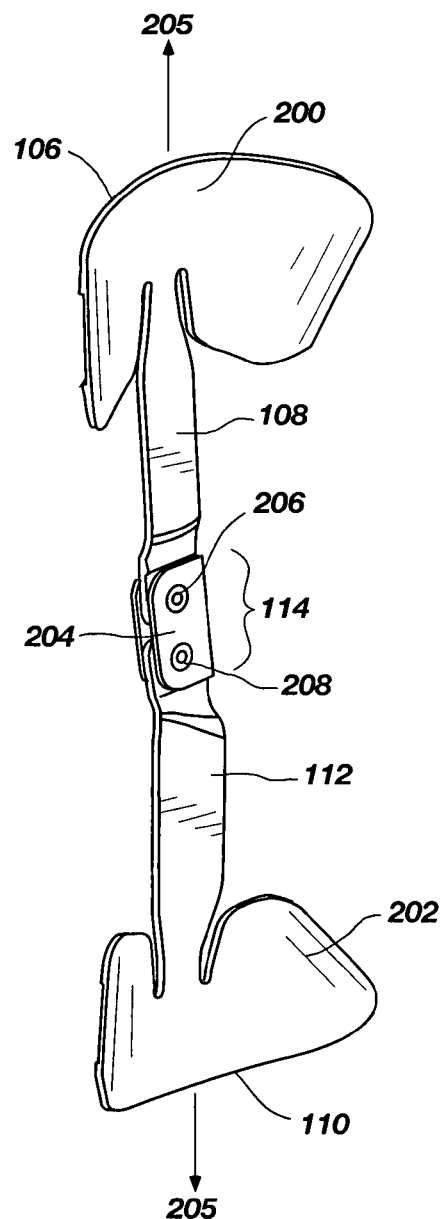
FIG. 2A
FIG. 2B

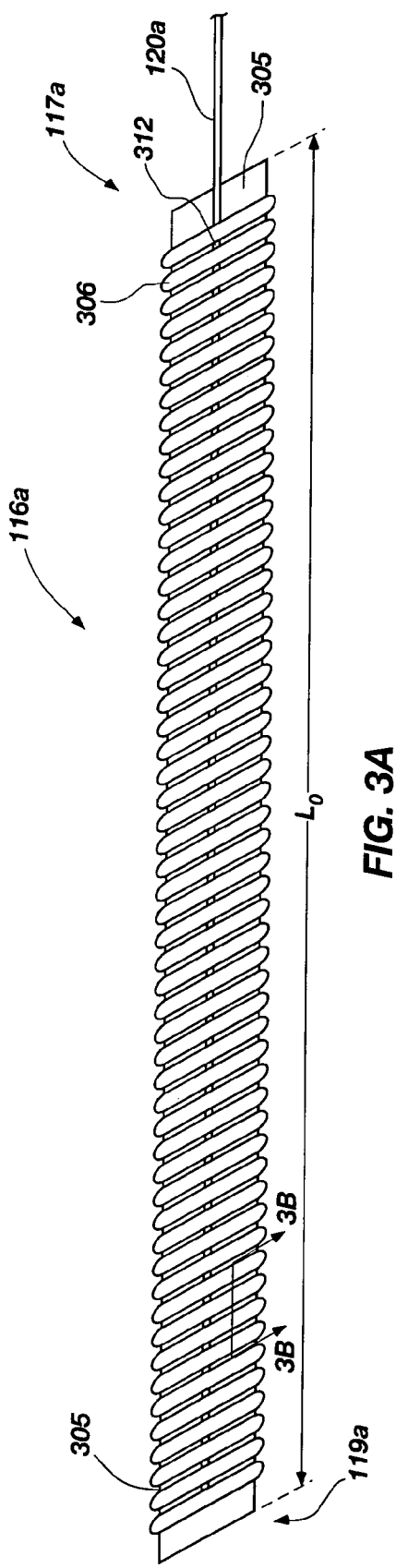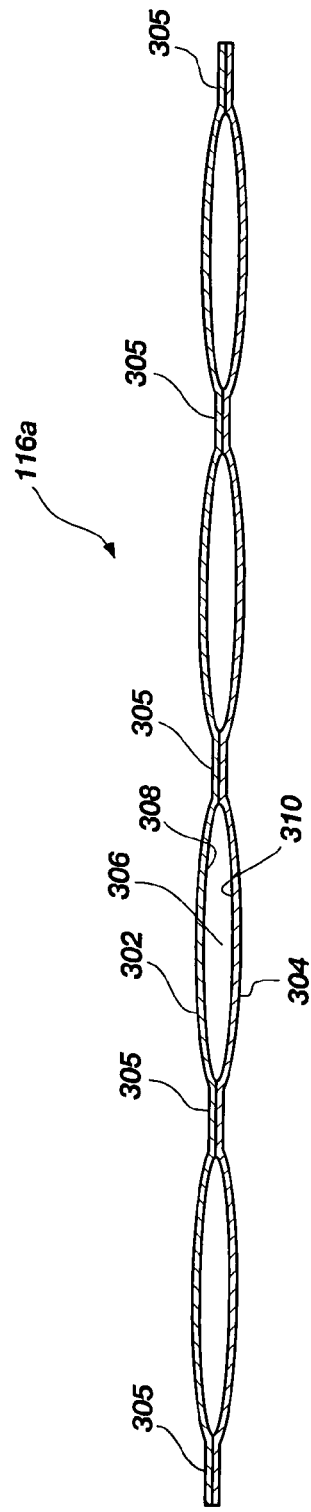
FIG. 3A
FIG. 3B

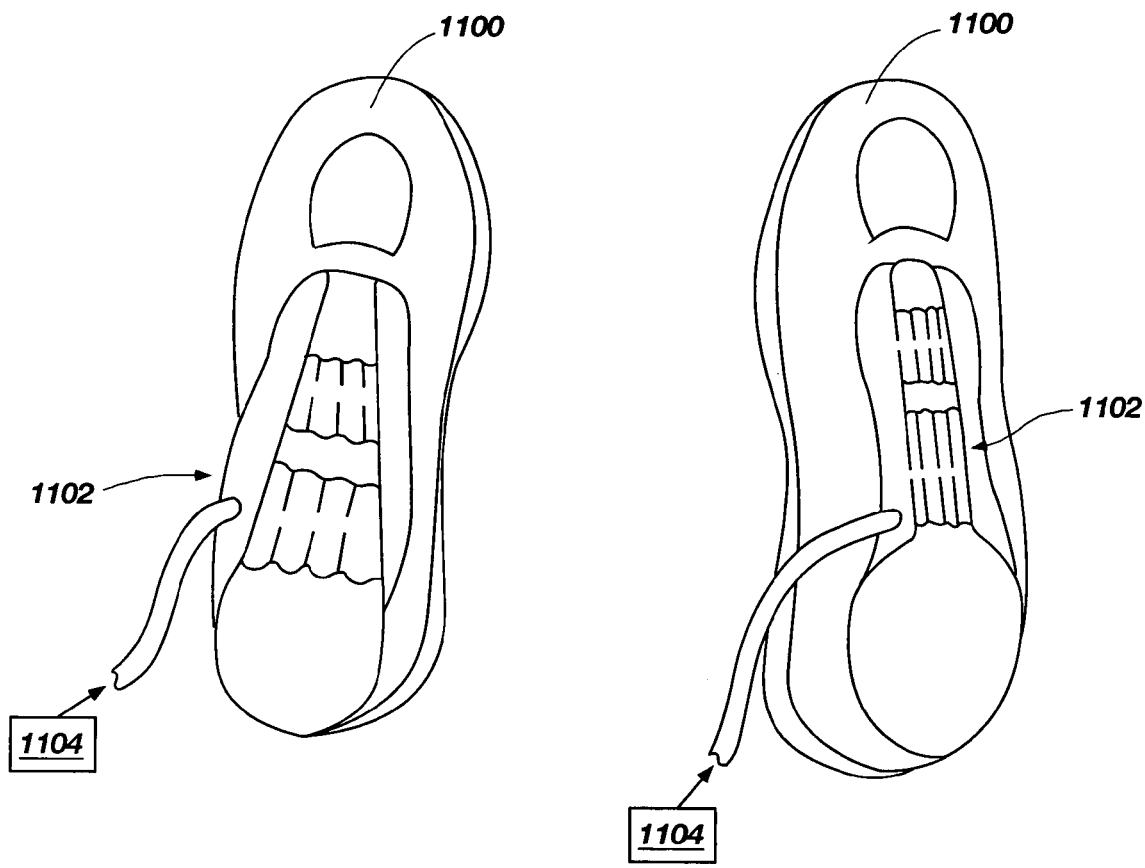
FIG. 11A　　　　FIG. 11B

ORTHOTIC APPARATUS AND METHOD OF OPERATION

CLAIM OF PRIORITY

This application claims priority from U.S. Provisional Application No. 60/931,300 filed on 22 May 2007, which is incorporated herein, in its entirety, by this reference.

BACKGROUND

A variety of knee braces are currently available for treating different knee problems. Knee braces may be designed to impart forces on limbs surrounding the knee to relieve compressive forces in a portion of the knee. Additionally, knee braces are often employed to support the knee after a knee injury, such as a sprain, or to assist with rehabilitation of the knee after a traumatic event, such as knee surgery.

The human knee is a joint held together by small, powerful ligaments. The femur (i.e., the thighbone) meets the tibia (i.e., the large shin bone) to form the main knee joint called the femoro-tibial joint. The kneecap (i.e., the patella) joins the femur to form a second joint called the femoro-patellar joint. The patella protects the front of the knee. The knee is surrounded by a joint capsule with collateral ligaments strapping the inside and outside of the joint and cruciate ligaments crossing within the joint. The collateral ligaments run along the sides of the knee and limit the sideways motion of the knee. The anterior cruciate ligament ("ACL") connects the tibia to the femur at the center of the knee and functions to limit rotation and forward motion of the tibia. The ACL divides the knee into an inner (medial) and an outer (lateral) compartment. The posterior cruciate ligament ("PCL") is located aft of the ACL and limits backward motion of the tibia. The knee also includes a thickened cartilage pad known as a meniscus attached to the tibia and an articular cartilage attached to the femur. The meniscus and articular cartilage function as smooth bearing surfaces that allow for pain-free relative rotation of the femur and tibia.

The knee is still a relatively weak joint that can be easily damaged despite the knee being held together by powerful ligaments. For example, the knee may be damaged by participating in sporting events, overloading due to obesity, aging, or misalignment of the knee. Most knee problems are a result of damage of the cartilage of the knee and strain of the ligaments of the knee.

One important knee problem is unicompartmental osteoarthritis in which either the medial (inward) or the lateral (outward) compartment of the knee joint is deteriorated. In a proper functioning knee, both compartments are loaded generally uniformly. A knee joint that suffers from unicompartmental osteoarthritis is characterized by an uneven distribution of pressure in either the medial or lateral compartment of the knee. Such uneven distribution of pressure can wear away the smooth cartilage lining the inside of the knee, which may, consequently, lead to painful, direct contact between the femur and the tibia.

Unicompartmental osteoarthritis may be treated by using a knee brace that is configured to urge the femur and tibia apart in the affected compartment of the knee to reduce or eliminate the painful bone-to-bone contact between the femur and the tibia. Despite the availability of a number of different knee braces to treat unicompartmental osteoarthritis, there is still a need for an improved knee or other joint brace to treat unicompartmental arthritis and/or other knee or joint problems.

SUMMARY

Various embodiments of the invention relate to orthotic apparatuses configured to apply a controllable, therapeutic force to a joint of a subject. In one embodiment of the invention, an orthotic apparatus includes a frame structure and an actuator system operable to provide input energy of a first type (e.g., fluid pumped by a pump or an applied voltage). At least one strap structure is attached to the frame structure and operably coupled to the actuator system. The at least one strap structure may be configured to convert at least a portion of the input energy to energy of a second type, the energy of the second type being strain energy.

In an embodiment, the actuator system includes a pump in fluid communication with the at least one strap structure and operable to pump fluid into the at least one strap structure. The at least one strap structure may further include a plurality of inflatable chambers spaced along a length of the at least one strap structure so that the length thereof decreases responsive to inflating the inflatable chambers with the fluid. In another embodiment, the at least one strap structure may include an electroactive polymer and the at least one strap structure may increase in length responsive to application of a voltage to the at least one strap structure. In yet another embodiment, the at least one strap structure may include a shape memory alloy that contracts in length responsive to heating.

Additional embodiments of the invention are directed to inflatable structures, such as inflatable strap structures, which may be used to apply a controllable force in an orthotic apparatus or in numerous other applications.

BRIEF DESCRIPTION OF THE DRAWINGS

The drawings illustrate various embodiments of the invention, wherein like reference numerals refer to like elements or features in different views or embodiments shown in the drawings.

FIG. 2A is a front perspective view of the frame structure shown in FIGS. 1A-1C according to one embodiment of the invention.

FIG. 2B is a rear perspective view of the frame structure shown in FIG. 2A.

FIG. 3A is a perspective view of one of the strap structures shown in FIGS. 1A-1C in a non-inflated state.

FIG. 3B is a partial cross-sectional view of the strap structure shown in FIG. 3A taken along line 3B-3B when the strap structure is partially inflated.

FIG. 11A is a perspective view of a shoe including an inflatable strap structure according to another embodiment.

FIG. 11B is a perspective view of the shoe of FIG. 11A when the inflatable strap structure is inflated.

DETAILED DESCRIPTION

Various embodiments of the invention are directed to orthotic apparatuses configured to apply a controllable, therapeutic force to a subject, and inflatable structures such as inflatable strap structures. The disclosed embodiments for orthotic apparatuses may utilize a number of different types of configurations for strap structures that apply a therapeutic force to, for example, a user's knee for alleviating pressure in a lateral or medial compartment of the knee for treating osteoarthritis of the knee, for alleviating other knee infirmities, or for generally supporting the knee or other joint. The disclosed orthotic apparatuses may also be used in applications other than for applying a load to a joint of a subject. The orthotic apparatuses may include a frame structure attached to at least one strap structure that is configured to convert at least a portion of input energy (e.g., fluid pumped by a pump or an applied voltage) provided by an actuator system to energy of a second type (i.e., strain energy) that may be manifested as a change in length of the at least one strap structure. For example, in an embodiment, the at least one strap structure may comprise an inflatable structure that contracts in length responsive to being inflated by a fluid pump. In another embodiment, the strap structures may comprise an electroactive polymer that increases in length responsive to an applied voltage. In yet another embodiment, the strap structures may include a shape memory alloy that contracts in length responsive to heating.

Figure 1A:
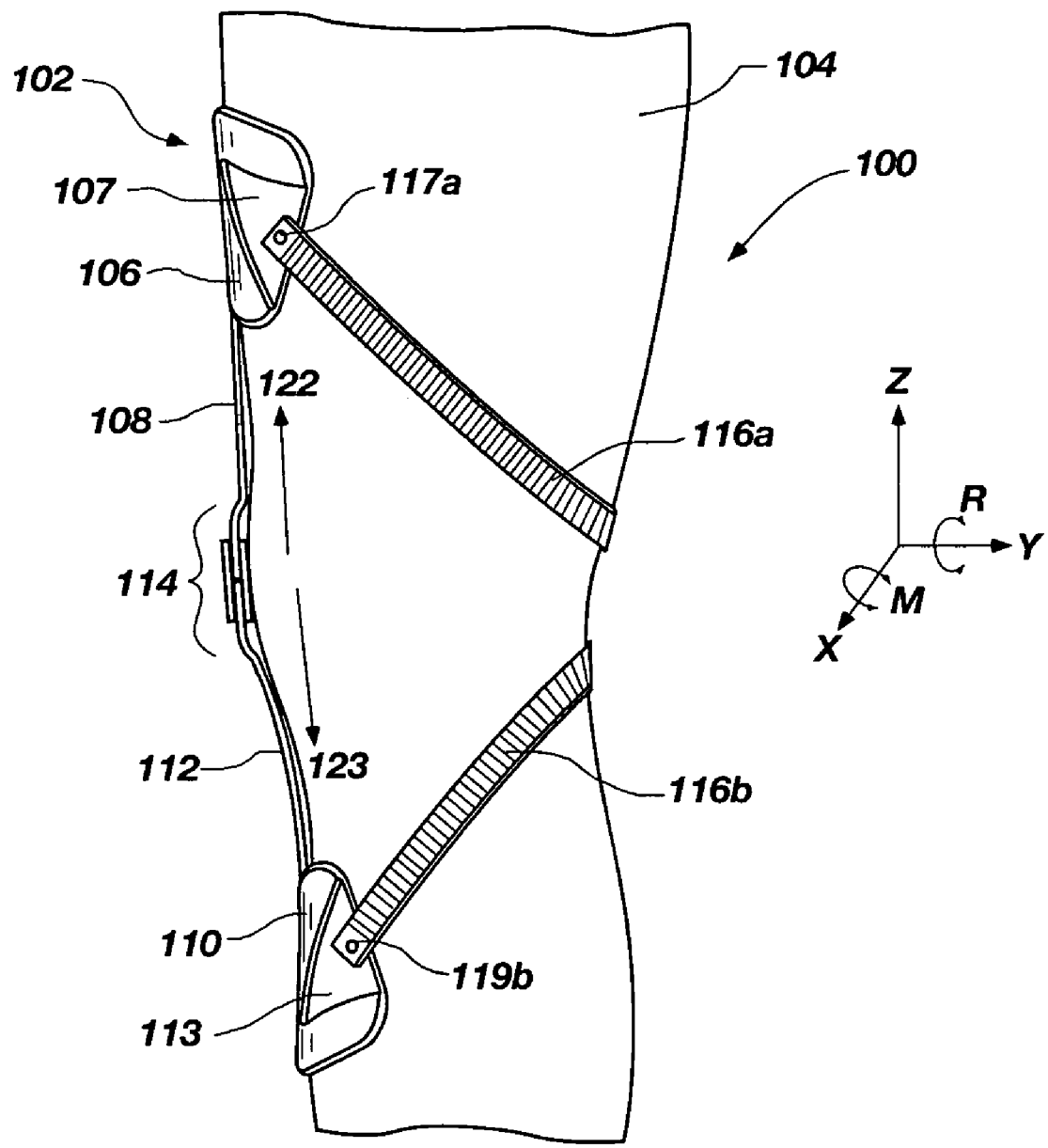
FIG. 1A is a perspective view taken from a back side of a user's leg illustrating an orthotic apparatus having a frame structure positioned on a medial side of a knee and inflatable strap structures for applying a therapeutic load to the knee according to one embodiment of the invention.
Figure 1B:
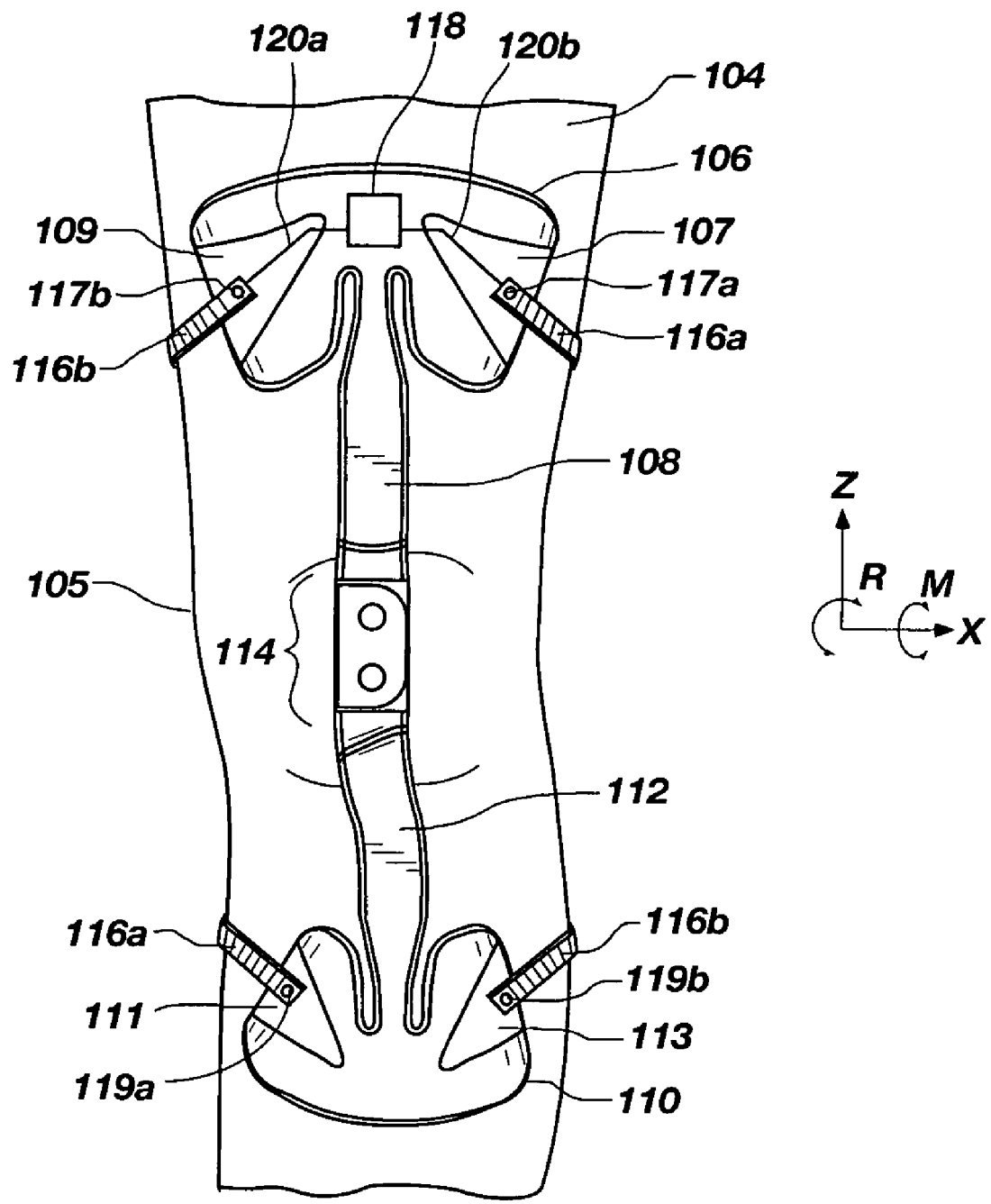
FIG. 1B is a perspective view of the orthotic apparatus shown in FIG. 1A taken from the medial side of the knee.
Figure 1C:
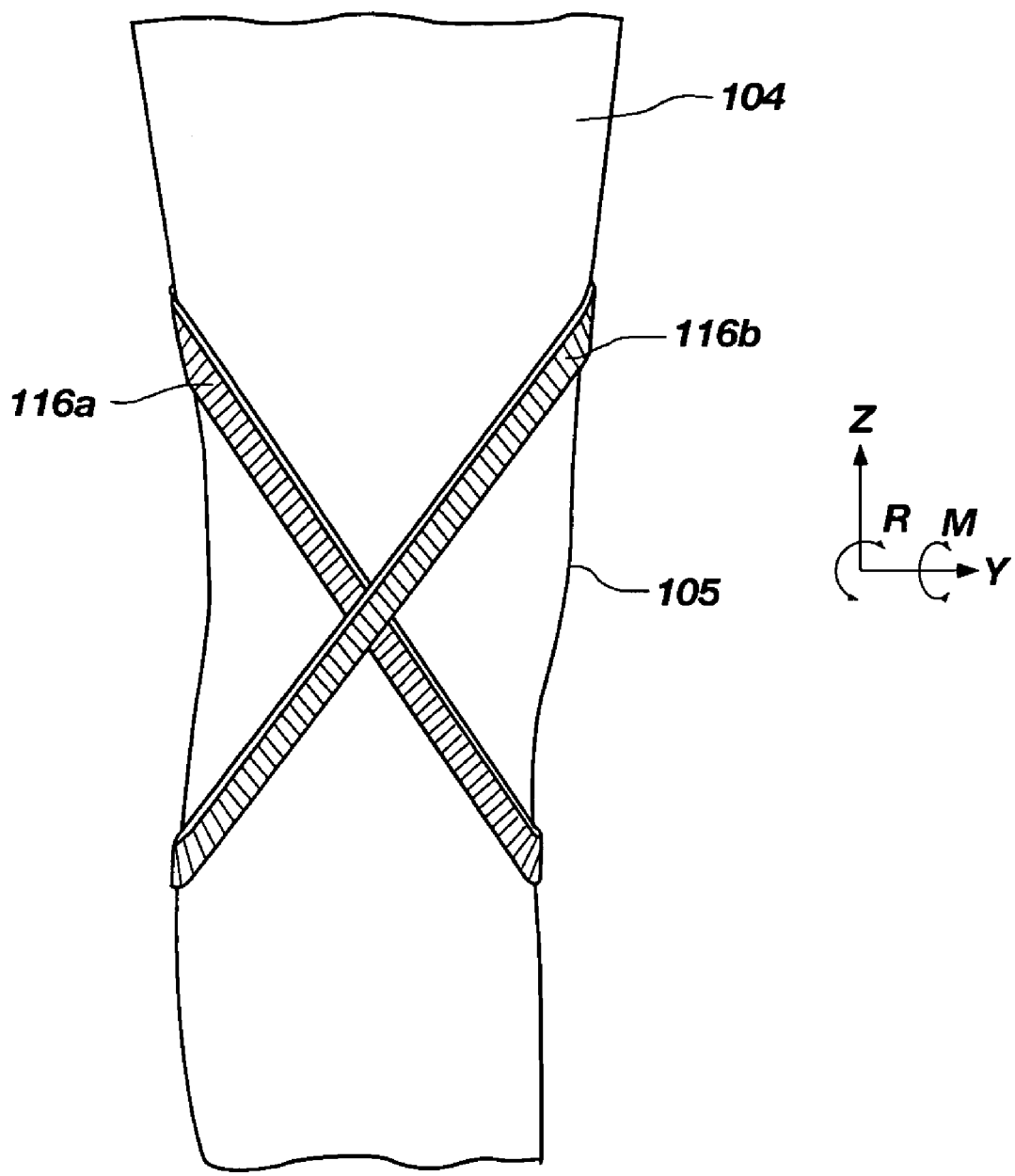
FIG. 1C is a perspective view of the orthotic apparatus shown in FIG. 1A taken from a lateral side of the knee.

FIGS. 1A-1C are perspective views of an orthotic apparatus 100 taken from a back side, a medial side, and a lateral side, respectively, of a user's leg according to one embodiment of the invention. The orthotic apparatus 100 includes at least one strap structure including a plurality of longitudinally spaced, inflatable chambers structured so that a length of the at least one strap structure may decrease responsive to inflating the inflatable chambers with a fluid to enable controllably tensioning the at least one strap structure. The orthotic apparatus 100 includes a frame structure 102 extending along a length of a user's leg 104, with the frame structure 102 positioned adjacent to a medial side of the user's knee 105. The frame structure 102 includes an upper shell 106 configured to generally conform to the user's leg 104 and an elongated support arm 108 extending from the upper shell 106. The frame structure 102 further includes a lower shell 110 that is also configured to generally conform to the user's leg 104 and an elongated support arm 112 extending toward the elongated support arm 108. The elongated support arms 108 and 112 may be hingedly connected to each other via a hinge assembly 114 to enable rotation relative to each other in a direction R when the user bends the knee 105.

The elongated support arms 108 and 112 and shells 106 and 110 may be formed from a number of different materials, such as engineering plastics, metallic materials, polymer-matrix composites, or another suitable material. In the illustrated embodiment, the elongated support arms 108 and 112 are integrally formed with the corresponding upper shell 106 and lower shell 110. However, in another embodiment, the elongated support arms 108 and 112 and the shells 106 and 110 may be separate pieces, with the upper shell 106 attached to the elongated support arm 108 and the lower shell 110 attached to the elongated support arm 112 using fasteners or another suitable technique. Additionally, in a further embodiment, the hinge assembly 114 may be omitted. In such an embodiment, the frame structure 102 may be a unitary piece that is configured to flex or bend with a selected stiffness as the user bends their knee 105. Thus, in such an embodiment, the upper shell 106 and elongated support arm 108 may move relative to the lower shell 110 and elongated supper arm 112 when the user bends their knee 105.

Figure 2C:
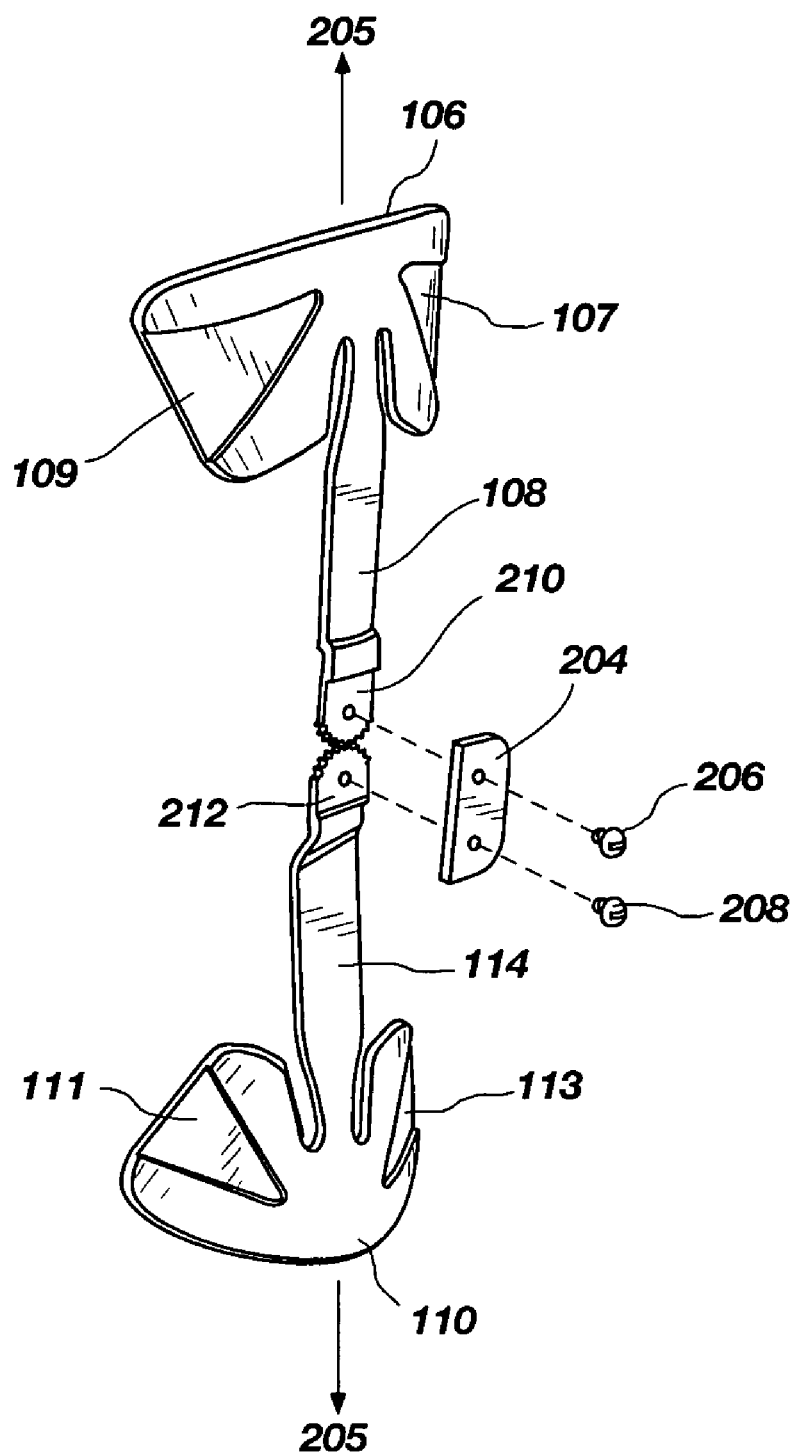
FIG. 2C is an exploded perspective view of the frame structure shown in FIGS. 2A and 2B that illustrates the hinge assembly of the frame structure in more detail.

FIGS. 2A-2C are front, rear, and exploded perspective views, respectively, of the frame structure 102 and the hinge assembly 114. As previously noted, the upper shell 106 and the lower shell 110 are configured to conform to the user's leg 104. Referring to FIG. 2B, the upper shell 106 has a surface 200 and the lower shell 110 has a surface 202, both of which are suitably concavely curved to enable conforming to the user's leg 104. Referring to FIG. 2C, the hinge assembly 114 includes a coupling member 204 that partially encloses a gear 210 located at a distal end of the elongated support arm 108, and a gear 212 located at a distal end of the elongated support arm 112. The coupling member 204 is secured to the elongated support arms 108 and 112 using fasteners 206 and 208 that are secured to the gears 210 and 212 and the coupling member 204. When assembled, the gears 210 and 212 mesh with each other. As previously discussed the hinge assembly 114 enables the elongated support arms 108 and 112 to be relatively rotated in the direction R (FIG. 1A) about an axis generally perpendicular to a longitudinal axis 205 of the frame structure 102. The elongated support arm 108 rotates about an axis (not shown) that passes through the fastener 206 and the elongated support arm 112 rotates about an axis (not shown) that passes through the fastener 208.

It should be emphasized that the frame structure 102 merely represents one embodiment of a suitable frame structure for the orthotic apparatus 100. Any suitable frame structure that is configured to rotate or bend with rotation of the user's knee 105 when the frame structure is secured to the user's leg 104 may be used. For example, the gears 210 and 212 may be omitted and the elongated support arms 108 and 112 may be pivotally connected to each other using a fastener. Furthermore, in any of the embodiments disclosed herein, a fabric sleeve may be provided that conceals the frame structure 102 and/or is attached to the frame structure 102, for example, using Velcro® straps or another suitable securing structure. The fabric sleeve may help properly position and maintain position, during use, of the frame structure 102 on the leg 104 of the user.

Turning again to FIGS. 1A-1C, the orthotic apparatus 100 includes inflatable strap structures 116a and 116b that secure the frame structure 102 on the user's leg 104. The structure and functionality of the strap structures 116a and 116b will be discussed in more detail below in FIGS. 3A-4B. The inflatable strap structure 116a has a proximal end 117a and a distal end 119a defining a length, with the proximal end 117a attached a side 107 of the upper shell 106 and the distal end 119a attached to a side 111 of the lower shell 110. The inflatable strap structure 116b has a proximal end 117b and a distal end 119b defining a length, with the proximal end 117b attached to the side 109 of the upper shell 106 and the distal end 119b attached to the side 113 of the lower shell 110. The inflatable strap structures 116a and 116b may be secured to the upper shell 106 and lower shell 110 using fasteners, such as rivets, screws, buttons, or other suitable fasteners.

Referring to FIG. 1C, the inflatable strap structures 116a and 116b may cross each other to form an "X" pattern. When the frame structure 102 is positioned on the medial side of the user's knee 105, the region at which the inflatable strap structures 116a and 116b cross each other is located adjacent to the lateral side of the user's knee 105. It is noted that while two strap structures are employed in the illustrated embodiment, in other embodiments, a single inflatable strap structure may be coiled in a manner to form the "X" pattern.

Referring again to FIG. 1B, the orthotic apparatus 100 further includes an actuator system 118 operably coupled to each of the inflatable strap structures 116a and 116b via corresponding fluid conduits 120a and 120b. The actuator system 118 is operable to controllably inflate and deflate the inflatable strap structures 116a and 116b. The inflatable strap structures 116a and 116b are configured so that when inflated the inflatable strap structures 116a and 116b each contract in length to apply a therapeutic force to the user's knee 105.

With reference to FIGS. 1A and 1C, inflating each of the inflatable strap structures 116a and 116b using the actuator system 118 causes the inflatable strap structures 116a and 116b to contract in length and, consequently become tensioned. Tensioning the inflatable strap structures 116a and 116b subjects the user's knee 105 to a generally three-point bending loading that applies a moment M to the user's knee 105. The moment M illustrated in FIGS. 1A and 1C is a varus moment that urges the femur and tibia apart generally in directions 122 and 123, respectively, to unload the affected medial compartment of the knee 105. Of course, the orthotic apparatus 100 may be positioned with the frame structure 102 on a lateral side of the user's knee 105. In such a case, tensioning of the inflatable structures 116a and 116b would apply a valgus moment to the user's knee 105 and urge the femur and tibia apart on the affected lateral compartment of the user's knee 105.

The structure and functionality of the inflatable strap structures 116a and 116b are best understood with reference in FIGS. 3A-3B and 4A-4B. It should be understood that the inflatable strap structure 116b may have the same or similar structure and functionality as the inflatable strap structure 116a shown in FIGS. 3A-3B and 4A-4B. Referring to FIGS. 3A and 3B, the inflatable strap structure 116a is shown in a minimally inflated state having a length $L_O$. The inflatable strap structure 116a may be formed from two pieces of sheet material 302 and 304 (FIG. 3B) that are joined together in selected regions represented as bond regions 305 to define a plurality of longitudinally spaced, elongated, inflatable chambers 306. The two pieces of sheet material 302 and 304 may each be formed from 200 Denier Nylon having, for example, a thickness of about 0.0010 inches to about 0.0020 inches, or another suitable material. In an embodiment, the pieces 302 and 304 may comprise Denier Nylon, with interior, opposing surfaces 308 (FIG. 3B) and 310 (FIG. 3B) of the pieces 302 and 304 coated with a urethane coating that may bond together by ultrasonic welding to form the bond regions 305. In other embodiments, the inflatable strap structure 116a may be formed from a single sheet of material that is appropriately cut, folded, and welded to form inflatable chambers. Each inflatable chamber 306 is in fluid communication with an adjacent inflatable chamber 306 via a conduit 312 (FIG. 3A). The inflatable strap structure 116a may be inflated by pumping fluid, such as air or another fluid medium, through the fluid conduit 120a and into the inflatable chamber 306 closest to the proximal end 117a.

Figure 4A:
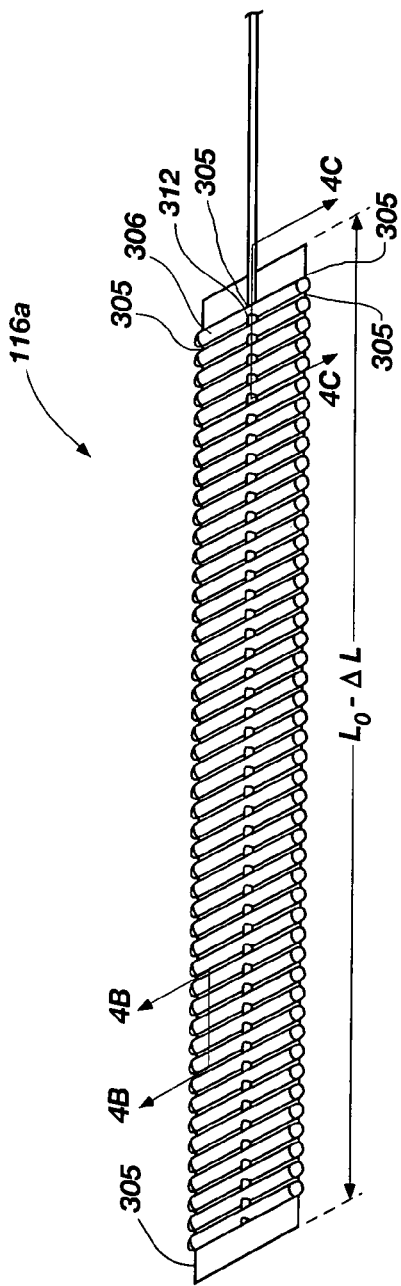
FIG. 4A is a perspective view of the strap structure shown in FIGS. 3A and 3B in an inflated state that illustrates how the strap structure contracts in length when inflated.

Referring to FIG. 4A, inflating the inflatable strap structure 116a converts the moving, fluid energy into strain energy that is manifested as a contraction in the length of the inflatable strap structure 116a. The inflatable strap structure 116a is structured to contract longitudinally to exhibit a length $L_O - \Delta L$ responsive to inflation of the inflatable chambers 306. The inflatable strap structure 116a gradually contracts in length as it is progressively inflated. Relieving internal pressure in the inflatable strap structure 116a allows the inflatable strap structure 116a to return to its initial un-strained length $L_O$. Representative maximum elastic strain (i.e., reversible deformation) for the inflatable strap structure 116a may be about 10 percent to about 20 percent longitudinal, elastic strain. Additionally, the longitudinal stiffness of the inflatable strap structure 116a varies depending upon the extent of inflation, with the stiffness of the inflatable strap structure 116a increasing as it is inflated. Because the inflatable strap structures 116a and 116b has a relatively large elastic strain range, the orthotic apparatus 100 may accommodate a wide range of leg sizes and geometries.

Figure 4B:
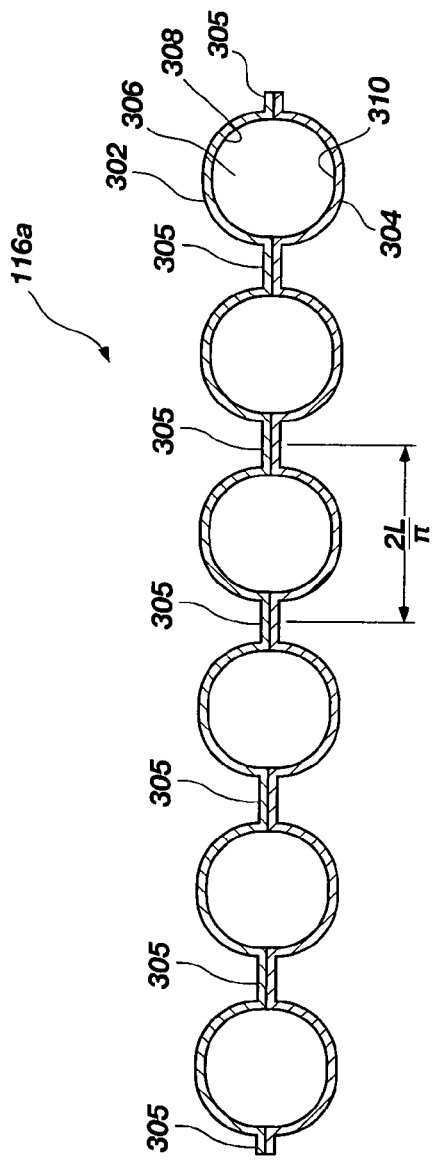
FIG. 4B is a partial cross-sectional view of the strap structure shown in FIG. 4A taken along line 4B-4B.
Figure 4C:
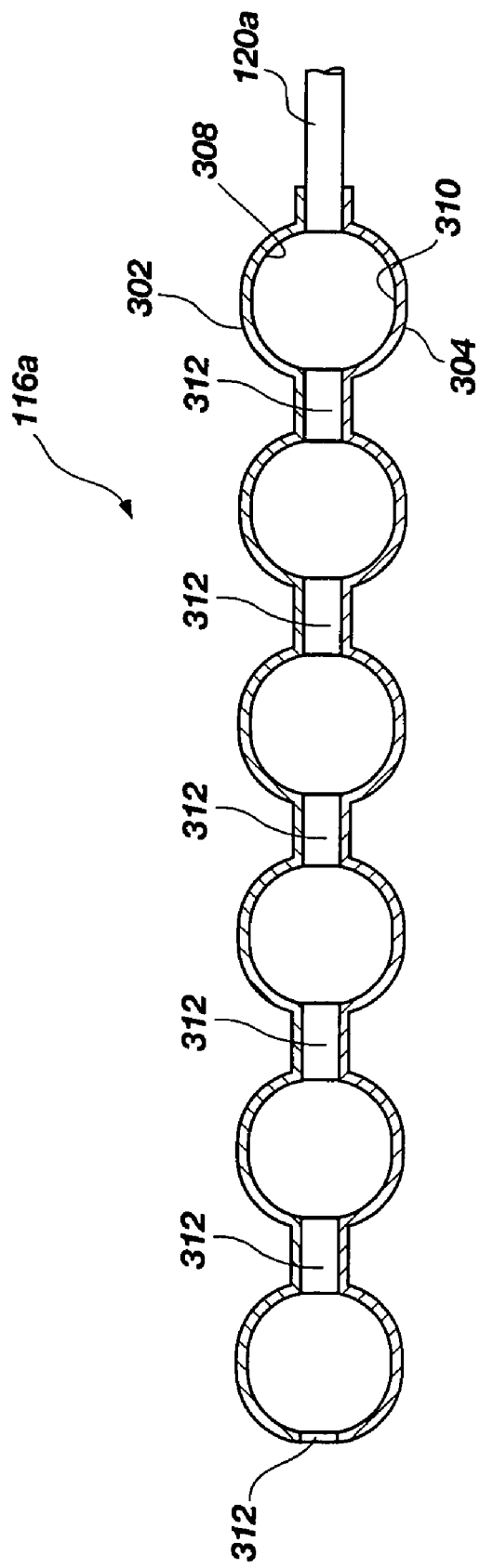
FIG. 4C is a partial cross-sectional view of the strap structure shown in FIG. 4A taken along line 4C-4C.

FIGS. 4B and 4C illustrate the internal structure of the inflatable strap structure 116a, when inflated, in more detail. FIG. 4B is a cross-sectional view of the inflatable strap structure 116a taken along line 4B-4B shown in FIG. 4A when inflated. Referring to FIG. 4B, the spacing between adjacent inflatable chambers 306 is about $2 L/\pi$, where L is the spacing between adjacent inflatable chambers 306 when the inflatable strap structure 116a is un-inflated. FIG. 4C is a cross-sectional view of the inflatable strap structure 116a, when inflated, taken along line 4C-4C shown in FIG. 4A that best illustrates how the multiple conduits 312 enable fluid communication between the inflatable chambers 306.

It should be noted that in some applications, the proximal end 117a and the distal end 119a of the inflatable strap structure 116a may be fixed in position relative to each other. In such applications, the overall length $L_O$ of the inflatable strap structure 116a may not change when the inflatable strap structure 116a is inflated. However, the arc length of the portions of the pieces 302 and 304 defining each of the inflatable chambers 306 may increase characteristic of an increase in strain energy of the inflatable strap structure 116a despite the overall length $L_O$ remaining relatively constant.

Figure 5:
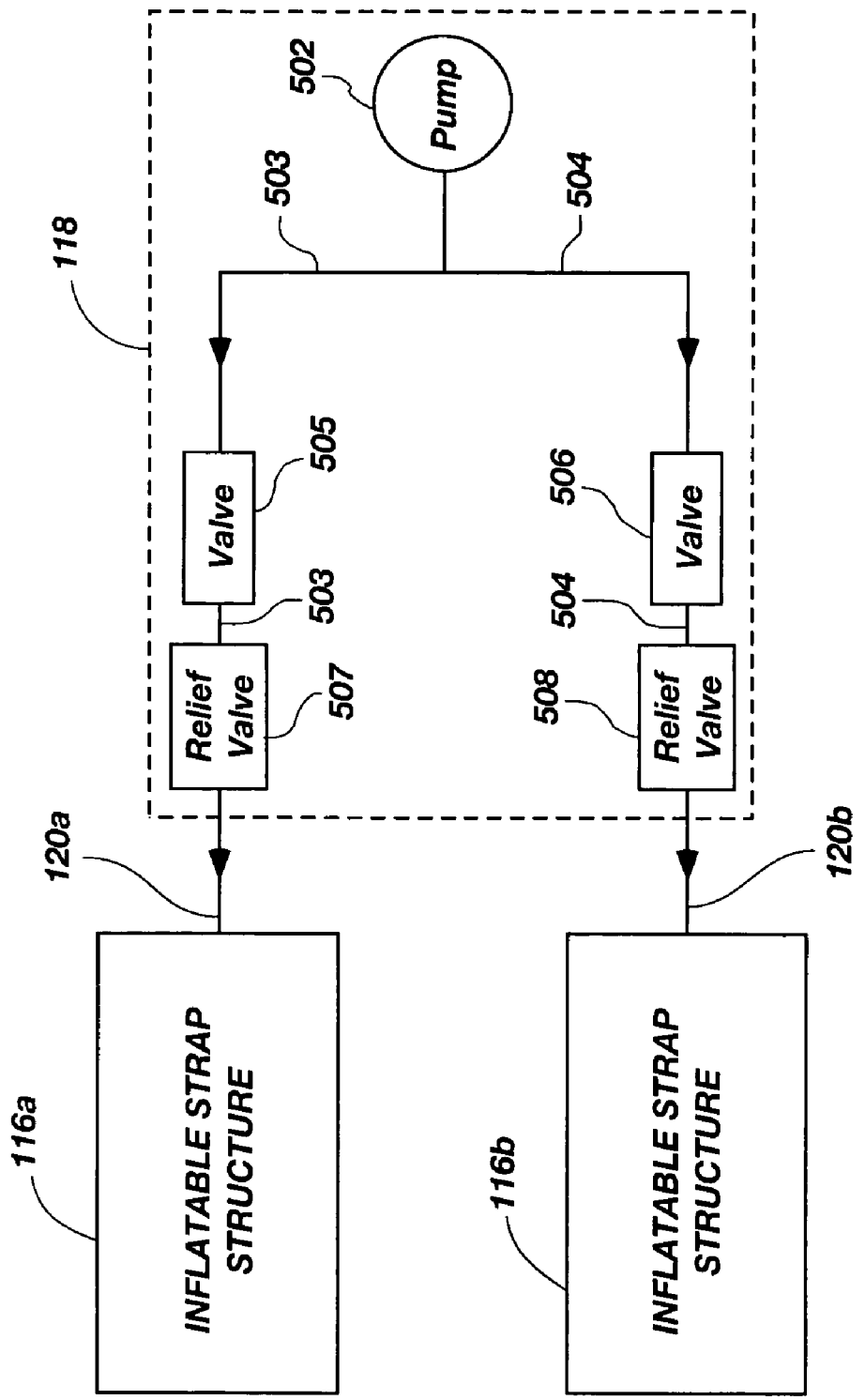
FIG. 5 is a functional block diagram of an embodiment of an actuator system operable to inflate and deflate the strap structures shown in FIGS. 1A-1C.

FIG. 5 is a functional block diagram that illustrates an embodiment for the actuator system 118 of the orthotic apparatus 100 shown in FIG. 1B. The actuator system 118 includes a pump 502 operably connected to fluid conduits 503 and 504.

One-way valves 505 and 506 may be in fluid communication with corresponding fluid conduits 503 and 504 to regulate the fluid flow therethrough. A relief valve 507 may be operably connected to the inflatable strap structure 116a and the fluid conduit 503 and a relief valve 508 may be operably connected to the inflatable strap structure 116b and the fluid conduit 504. The fluid conduits 120a and 120b (also shown in FIG. 1B) may be in fluid communication with the corresponding relief valves 507 and 508. In some embodiments, the pump 502 may be a manual pump, an electro-mechanical pump, or another suitable pump operable to pump air or another fluid medium to controllably inflate the inflatable strap structures 116a and 116b. For example, compact and light-weight electromechanical pumps that employ a bellows formed from an electroactive polymer are commercially available from Artificial Muscle, Inc. of Menlo Park, Calif.

In operation, the user may don the orthotic apparatus 100 (FIG. 1A) when the inflatable strap structures 116a and 116b are not inflated or are not inflated to an extent that prevents donning. The user may actuate the pump 502 by, for example, grasping and compressing a bellows of a manual pump or pressing a button or other user interface to actuate an electromechanical pump. The pump 502 pumps air or other fluid medium through the fluid conduits 503 and 504, one-way valves 505 and 506, relief valves 507 and 508, and fluid conduits 120a and 120b to controllably inflate the inflatable strap structures 116a and 116b to thereby tension the inflatable strap structures 116a and 116b. As previously described in FIGS. 1A-1C, tensioning the inflatable strap structures 116a and 116b applies a therapeutic moment to the user's knee that urges the user's femur and tibia apart. When the user desires to lower the tension on the inflatable strap structures 116a and 116b, the user may relieve pressure within the inflatable strap structures 116a and 116b by manually actuating the relief valves 507 and 508.

Figure 6:
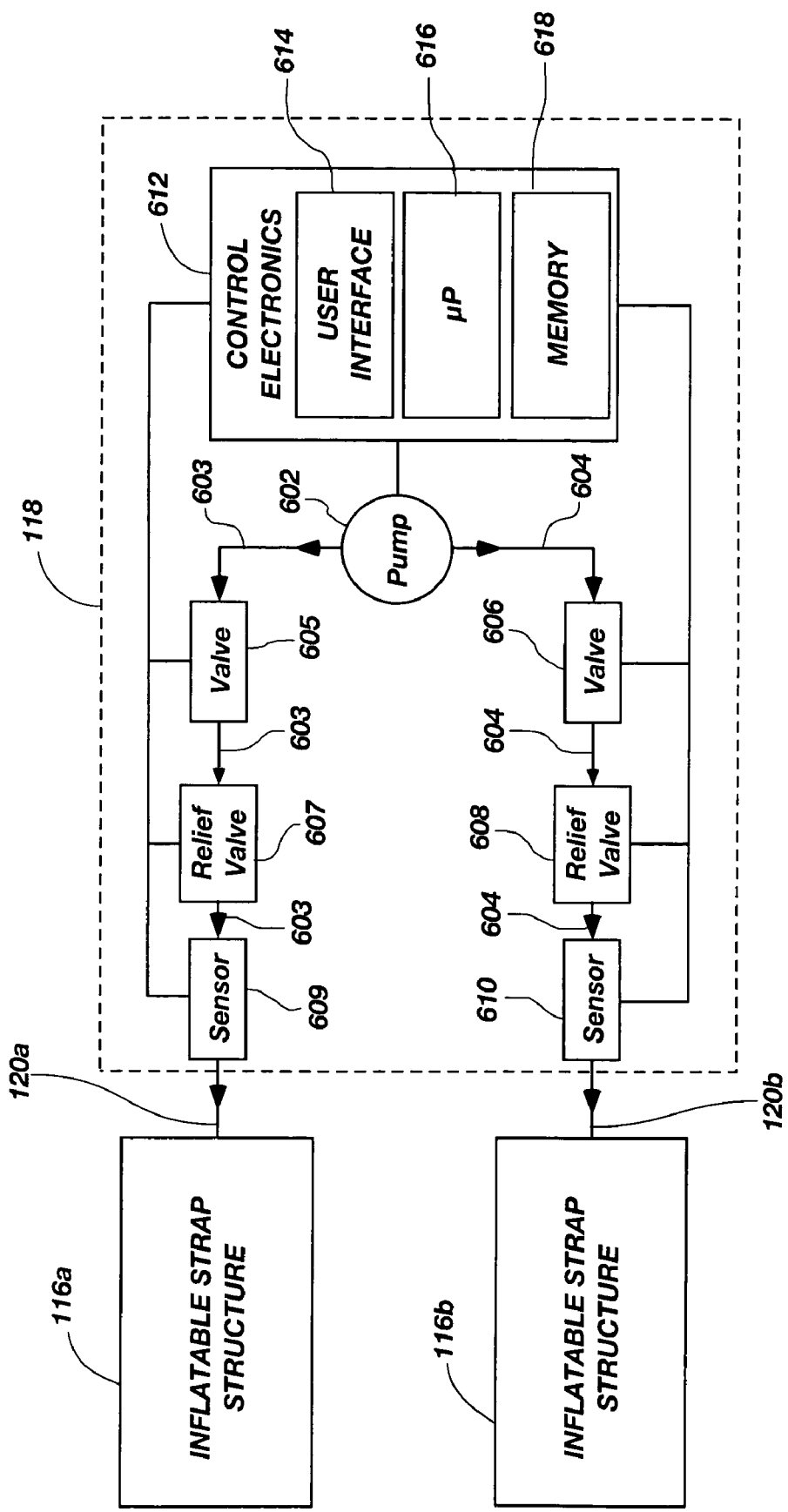
FIG. 6 is a functional block diagram of an embodiment of an actuator system that includes a pump and control electronics operable to control inflation and deflation of the strap structures shown in FIGS. 1A-1C.

FIG. 6 is a functional block diagram that illustrates another embodiment for the actuator system 118 of the orthotic apparatus 100 shown in FIG. 1B. The actuator system 118 includes a pump 602 (e.g., an electro-mechanical pump) operably connected to fluid conduits 603 and 604. Electronically-controlled, one-way valves 605 and 606 may be in fluid communication with corresponding fluid conduits 603 and 604 to regulate fluid flow through the fluid conduits 603 and 604. An electronically-controlled relief valve 607 may be operably coupled in series with the one-way valve 605 and an electronically-controlled relief valve 608 may be operably coupled in series with the one-way valve 606. A pressure sensor 609 may be connected in series with the relief valve 607 and valve 605, and a pressure sensor 610 may be connected in series with the relief valve 608 and valve 606. Each pressure sensor 609 and 610 may be, for example, a pressure transducer configured to determine pressure in corresponding fluid conduits 603 and 604 to be pumped into corresponding inflatable strap structures 116a and 116b. The fluid conduits 120a and 120b (also shown in FIG. 1B) may be in fluid communication with the corresponding fluid conduits 603 and 604.

The actuator system 118 may further include control electronics 612 having a user interface 614 (e.g., a keypad, a touch screen, etc.), a microprocessor ("µP") 616 that receives instructions from the user interface 614, and memory 618 for, optionally, storing operational settings to be executed by the microprocessor 616 and pressure data sensed by the pressure sensors 609 and 610. The control electronics 612 are operably coupled to the pump 602, one-way valves 605 and 606, relief valves 607 and 608, and sensors 609 and 610 to control the inflation and deflation of the inflatable strap structures 116a and 116b. For example, the microprocessor 616 may control the operation of the pump 602, one-way valves 605 and 606, and relief valves 607 and 608 responsive to user input via the user interface 614, and both the microprocessor 616 and memory 618 may further receive pressure data from the sensors 609 and 610.

In operation, the user may input a desired tension level for the inflatable strap structures 116a and 116b using the user interface 614. Responsive to the user input, the pump 602 pumps air or other fluid medium through the fluid conduits 603 and 604 and into the fluid conduits 120a and 120b that are in fluid communication with corresponding inflatable strap structures 116a and 116b to cause inflation thereof. Pressure within the fluid conduits 603 and 604 may be determined by the pressure sensors 609 and 610 and transmitted to the control electronics 612. The pressure within the fluid conduits 603 and 604 is indicative, although not the same, as the pressure within the inflatable strap structures 116a and 116b. Thus, the actuator system 118 may be calibrated so that specific line pressures in the fluid conduits 603 and 604 correspond to specific tensions in the inflatable strap structures 116a and 116b.

In an embodiment, when the tension in the inflatable strap structures 116a and 116b is not at the user's desired level, the microprocessor 616 may instruct the pump 602 to pump additional fluid through the fluid conduits 603 and 604 and into the inflatable strap structures 116a and 116b. When the tension in the inflatable strap structures 116a and 116b is higher than the user's desired tension, the microprocessor 616 may instruct the relief valves 607 and 608 to open in order to relieve pressure in the corresponding inflatable strap structures 116a and 116b. The relief valves 607 and 608 continue to relieve pressure in the inflatable strap structures 116a and 116b until the sensors 609 and 610 measure that the pressure in the fluid conduits 603 and 604 is at a level that corresponds with the user's desired tension level in the inflatable strap structures 116a and 116b.

In an embodiment, the control electronics 612 may be configured to maintain a specific pressure within the inflatable strap structures 116a and 116b that corresponds to a specific, user selected, tension for the inflatable strap structures 116a and 116b that the user selects via the user interface 614. For example, during use, the orthotic apparatus 100 (FIG. 1A) may move on the user's leg 104 (FIG. 1A) and pressure within the inflatable strap structures 116a and 116b may decrease or increase. The microprocessor 616 may instruct the relief valves 607 and 608 to relieve pressure within the inflatable strap structures 116a and 116b or increase the pressure within the inflatable strap structures 116a and 116b by directing the pump 602 to pump additional fluid into the inflatable strap structures 116a and 116b responsive to pressure data from the sensors 609 and 610. In an embodiment, the memory 618 may store the pressure data from the sensors 609 and 610, and the control electronics 612 may include an output port (not shown) for downloading the pressure data to, for example, a desktop computer for analysis by a medical professional via a wired or wireless connection.

In yet another embodiment, the microprocessor 616 may be configured with a plurality of different operational settings, which the user may program through the user interface 614. For example, the microprocessor 616 may be programmed with a first operational setting that maintains the tension of the inflatable strap structures 116a and 116b at a first tension level that is suitable for low-intensity activities, such as walking. The microprocessor 616 may also be programmed with a second operational setting that maintains the tension of the inflatable strap structures 116a and 116b at a second tension level that is greater than the first tension level and suitable for high-intensity activities, such as sport activities. The user may selectively switch between the operational settings using the user interface 614. Moreover, in an embodiment, responsive to pressure data from the sensors 609 and 610, the microprocessor 616 may automatically switch between the different operational settings without user input. For example, when the pressure in the inflatable strap structures 116a and 116b has substantially increased or periodically increases over a selected time period characteristic of high-intensity activities, the microprocessor 616 may cause the tension in the inflatable strap structures 116a and 116b to increase by instructing the pump 602 to increase the pressure therein. In other embodiments, an accelerometer (not shown) may be used in addition to or as an alternative to the sensors 609 and 610 to sense the user's activity level has change and the tension in the inflatable strap structures 116a and 116b should be adjusted.

In some embodiments, the pressure sensors 609 and 610 may be replaced with strain gages, tension transducers, or another suitable measurement device. For example, each inflatable strap structure 116a and 116b may have a strain gage mounted thereto for determining the tension of the inflatable strap structures 116a and 116b, with each strain gage operably coupled to the control electronics 612.

Figure 7:
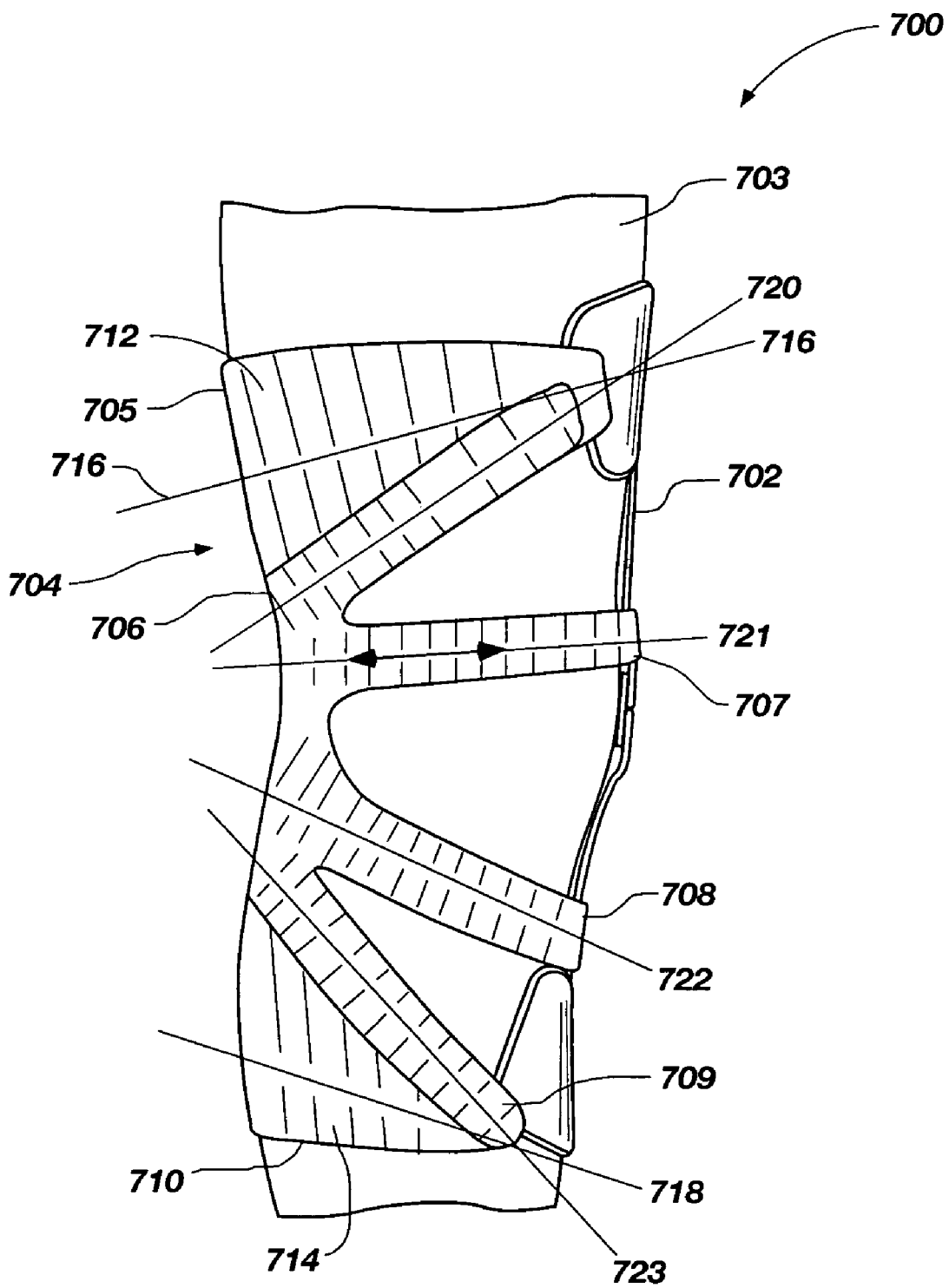
FIG. 7 is a perspective view of an orthotic apparatus, according to another embodiment, including multiple inflatable strap structures operable to apply specific therapeutic loads to a user's leg and/or knee.

Referring to FIG. 7, multiple inflatable strap structures similar to the inflatable strap structures 102a and 102b used in the orthotic apparatus 100 may comprise a larger structure for securing a frame structure on user's leg and/or applying specific therapeutic loads to the user's leg and knee. FIG. 7 is a perspective view of an orthotic apparatus 700 according to another embodiment. The orthotic apparatus 700 includes a frame structure 702 having the same or similar construction as the frame structure 102 shown in FIG. 1A-1C. The orthotic apparatus 700 further includes an inflatable structure or assembly 704 attached to the frame structure 702 that may comprise inflatable-strap-structure portions 705-710. For example, the inflatable-strap-structure portion 705 includes a plurality of spaced inflatable chambers 712 and the inflatable-strap-structure portion 710 also includes a plurality of inflatable chambers 714. Inflation of the inflatable-strap-structure portions 705 and 710 causes the inflatable-strap-structure portions 705 and 710 to contract generally along paths 716 and 718, respectively, thereby applying a therapeutic compression force to a user's leg 703. The inflatable-strap-structure portions 706-709 also include multiple inflatable cambers and may be similarly inflated to cause the inflatable-strap-structure portions 706-709 to contract generally along paths 720-723. Contraction of the inflatable-strap-structure portions 706-709 may be used to apply a therapeutic varus or valgus moment to a user's knee, as previously described, in order to relieve pressure in an affected compartment of the user's knee. Although not illustrated, the orthotic apparatus 700 may include an actuator system that is operable to individually and selectively inflate each of the inflatable-strap-structure portions 705-710. In other embodiments, the actuator system (not shown) may inflate each inflatable-strap-structure portion 705-710 substantially simultaneously.

In an embodiment, each inflatable-strap-structure portion 705-710 may be a separate inflatable structure, fabricated in the same or similar manner as the strap structures 102a and 102b shown in FIGS. 3A-4B. In other embodiments, each inflatable-strap-structure portion 705-710 may form part of a larger inflatable structure in which each inflatable-strap-structure portion 705-710 may be operationally isolated from each other so that they can be selectively and individually inflated. For example, the inflatable structure or assembly 704 may be formed from one or more pieces of Denier Nylon that are appropriately cut and welded to define the inflatable chambers and, if desired, to operationally isolate each of the inflatable strap structures 705-710.

Figure 8A:
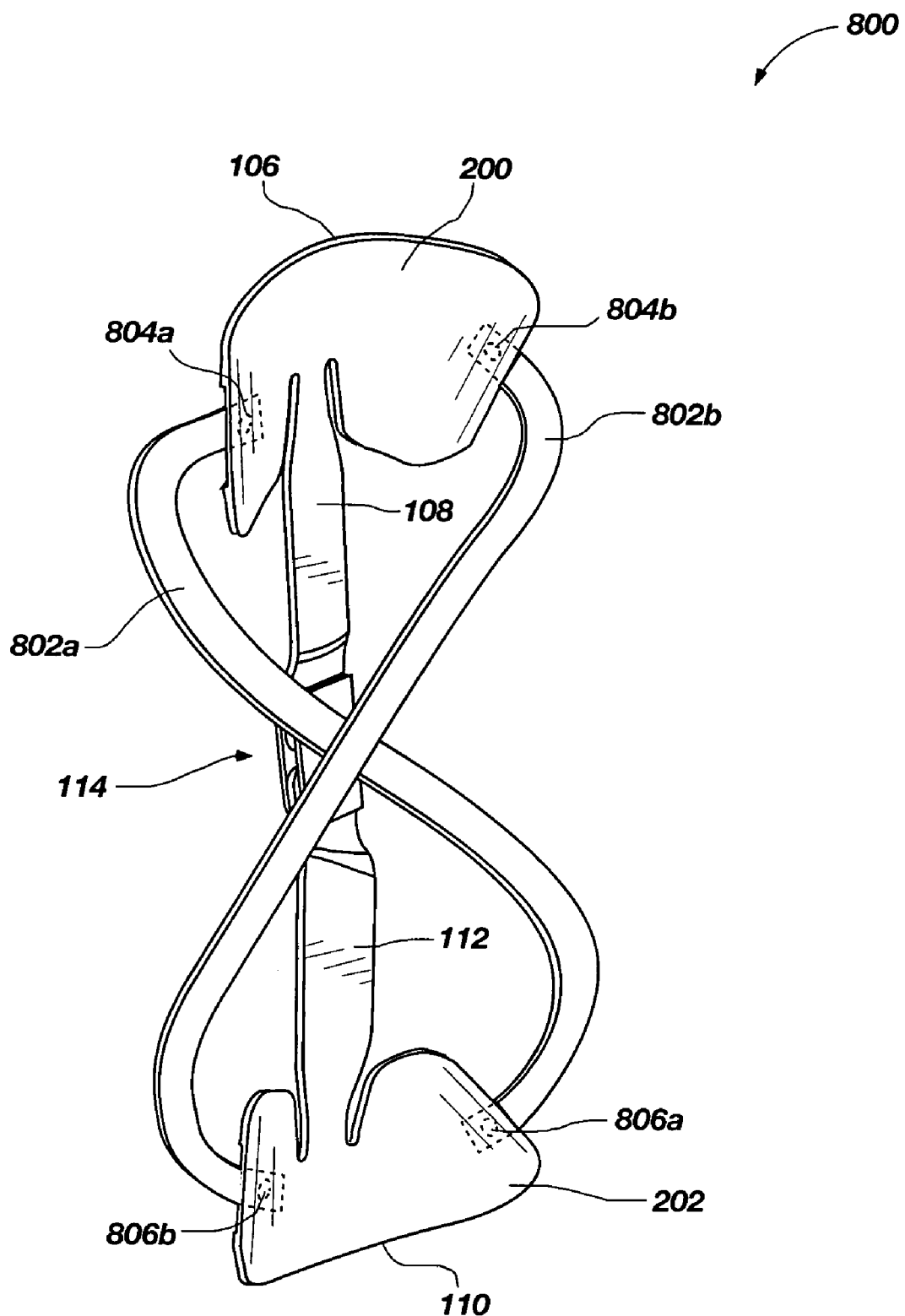
FIG. 8A is a rear perspective view of an orthotic apparatus including at least one strap structure having an electroactive polymer core according to an embodiment.
Figure 8B:
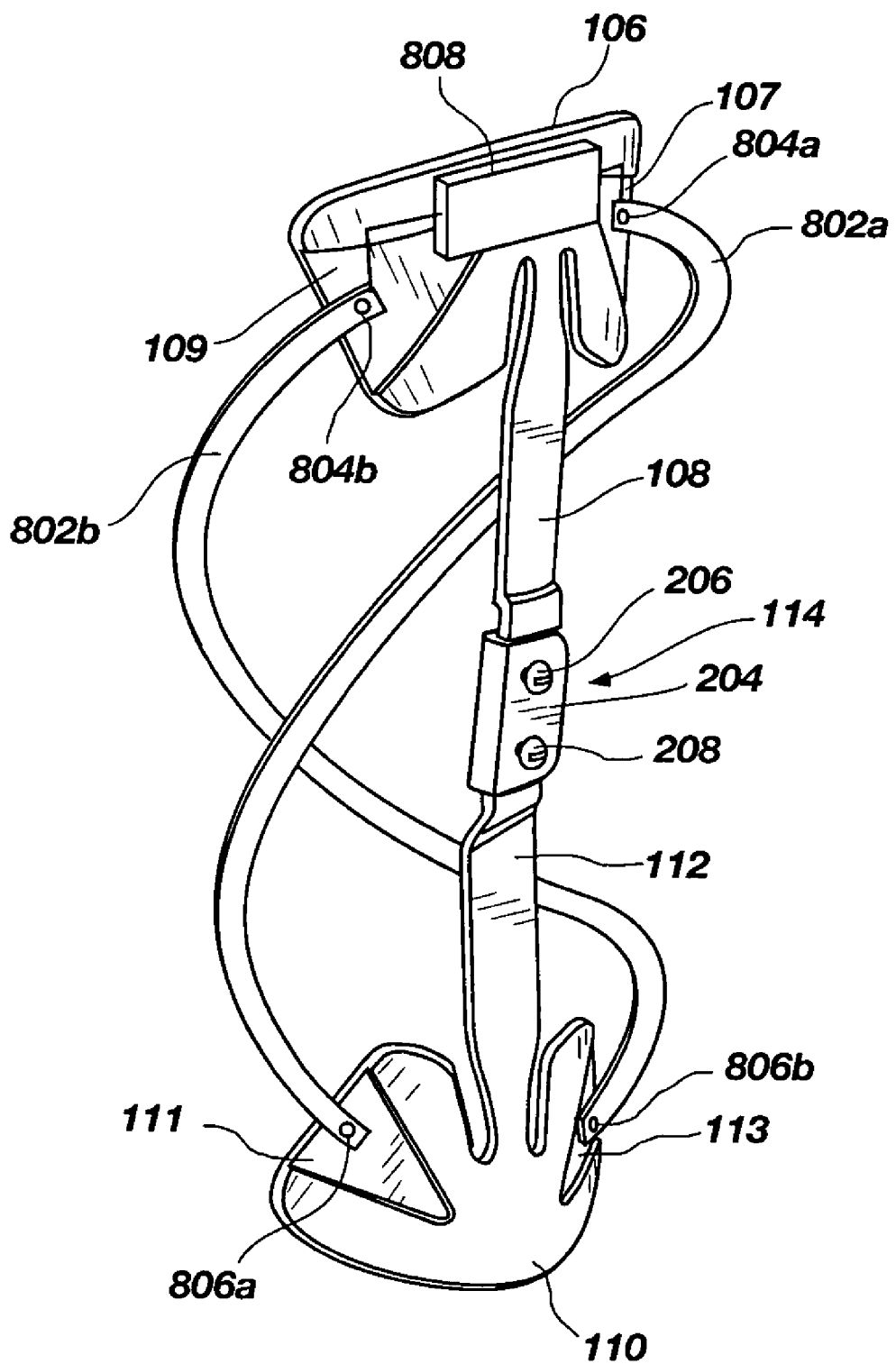
FIG. 8B is a front perspective view of the orthotic apparatus shown in FIG. 7A.

FIGS. 8A and 8B are rear and front perspective views, respectively, of an orthotic apparatus 800 according to another embodiment. As will be discussed in more detail below, the orthotic apparatus 800 utilizes strap structures 802a and 802b that each includes an electroactive polymer, with the length of the strap structures 802a and 802b controllable by application of a selected voltage to the electroactive polymer. In the interest of brevity, the strap structures 802a and 802b are attached to the same frame structure 102 shown in the orthotic apparatus 100 of FIGS. 1A-1C and FIGS. 2A-2C. Therefore, components in both orthotic apparatuses 100 and 800 that are identical to each other have been provided with the same reference numerals, and an explanation of their structure and function will not be repeated unless the components function differently in the two orthotic apparatuses 100 and 800.

Still referring to FIGS. 8A and 8B, the strap structures 802a and 802b are attached to the frame structure 102. The strap structure 802a has a proximal end 804a and a distal end 806a, with proximal end 804a attached to the side 107 of the upper shell 106 of the frame structure 102 and the distal end 806a attached to the side 111 of the lower shell 110 of the frame structure 102. The strap structure 802b has a proximal end 804b and a distal end 806b, with proximal end 804b attached to the side 109 of the upper shell 106 of the frame structure 102 and the distal end 806b attached to the side 113 of the lower shell 110 of the frame structure 102. The strap structures 802a and 802b cross each other to form an "X" pattern similar to the manner in which the inflatable strap structures 116a and 116b shown in FIGS. 1A-1C cross each other.

Figure 9A:
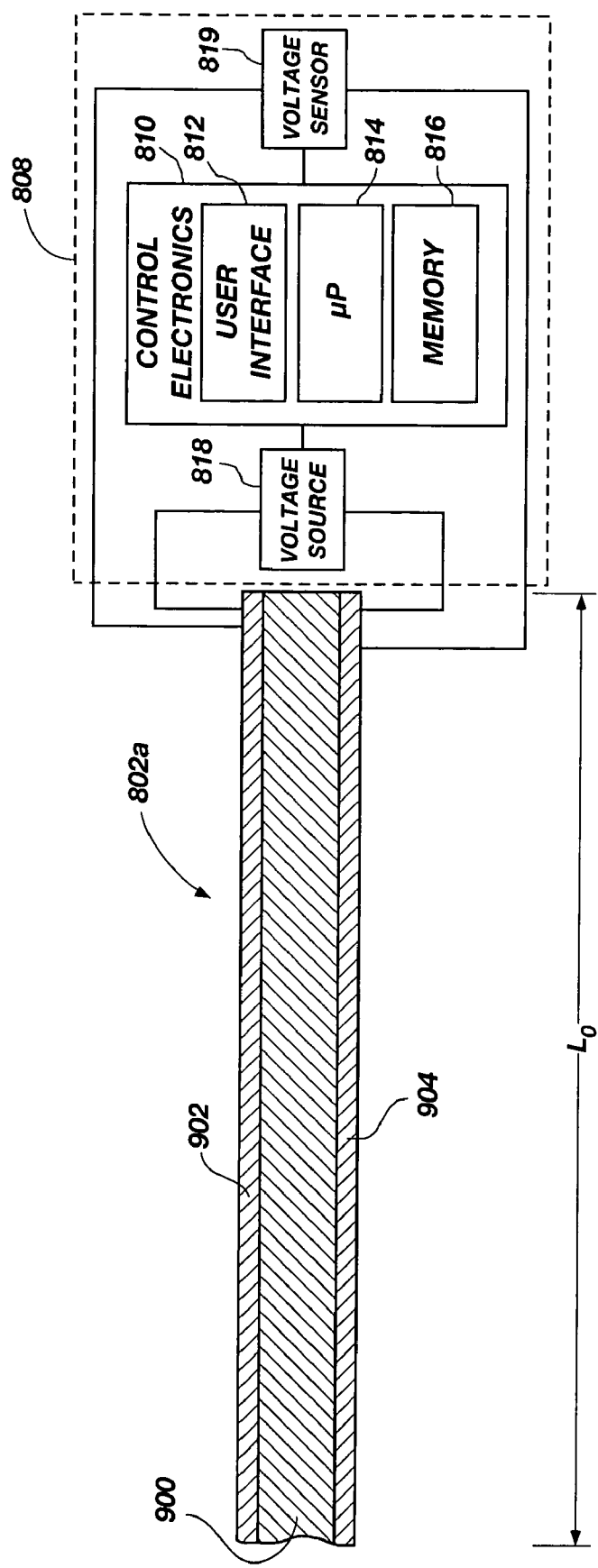
FIG. 9A is a functional block diagram of an embodiment of an actuator system operably coupled to one of the strap structures shown in FIGS. 8A and 8B, which is illustrated as a partial, longitudinal cross-sectional view, when a selected voltage is applied across the electroactive polymer core of the strap structure using the actuator system.
Figure 9B:
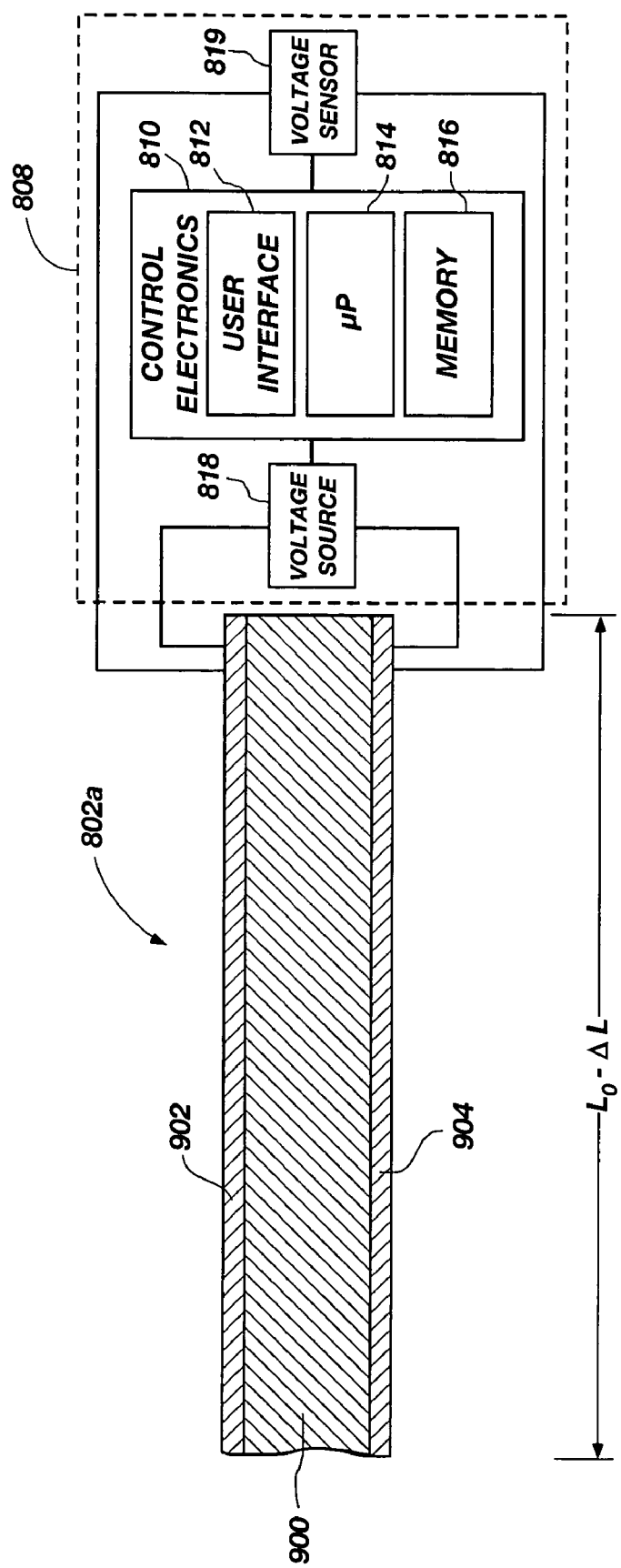
FIG. 9B is the functional block diagram of the actuator system and partial, longitudinal cross-sectional view of one of the strap structure shown in FIG. 8A when a magnitude of the selected voltage applied across the electroactive polymer core is reduced so that the length of the strap structure decreases.

Referring to FIGS. 9A and 9B, the orthotic apparatus 800 also includes an actuator system 808 that may include control electronics 810 having a user interface 812 (e.g., a keypad, touch screen, etc.), a microprocessor 814 that receives instructions from the user interface 812, and memory 816 for, optionally, storing operational settings to be executed by the microprocessor 814. The actuator system 808 further includes a voltage source 818 operably coupled to the microprocessor 814. The voltage source 818 is operable to apply a selected voltage across a thickness of each of the strap structures 802a and 802b responsive to instructions from the microprocessor ("μP") 814 to control the length of the strap structures 802a and 802b and, consequently, the tension of the strap structures 802a and 802b. In some embodiments, the actuator system 808 may also include a voltage sensor 819 operably coupled to the strap structures 802a and 802b to determine a voltage across each strap structure 802a and 802b, and coupled to the microprocessor 814 and the memory 816 to transmit voltage data thereto.

Still referring to FIGS. 9A and 9B, the structure of the strap structures 802a and 802b and the manner in which the actuator system 808 may control the length of the strap structures 802a and 802b is described. FIG. 9A only shows a portion of the strap structure 802a. However, the strap structure 802b may have the same or similar structure and functionality as the illustrated strap structure 802a, and the strap structure 802b may be operably coupled to the actuator system 808 in the same or similar manner as the strap structure 802a. The strap structure 802a is illustrated when the strap structure 802a is in an elastically deformed, elongated state with an initial length $L_O$ so that user may easily don the orthotic apparatus 800 on their leg. The strap structure 802a includes an electroactive polymer core 900 sandwiched between electrodes 902 and 904 that are in electrical contact with the electroactive polymer core 900. Electroactive polymers of the type used in the electroactive polymer core 900 may elastically increase in length by at least about 10 percent to about 20 percent by application of an electric field and return to their original length upon removal of the electric field. An electroactive polymer contracts in a direction generally parallel to the applied electric field and expands in a direction generally perpendicular to the applied electric field.

The electroactive polymer core 900 may be formed from a number of different commercially available electroactive polymers, such as ferroelectric polymers, dielectric elastomers, and electrostrictive graft elastomers. For example, suitable electroactive polymers for the electroactive polymer core 900 include, but are not limited to, NuSil CF19-2186 commercially available from NuSil Technology of Carpenteria, Calif., silicone elastomers, acrylic elastomers (e.g., VHB 4910 acrylic elastomer commercially available from 3M Corporation of St. Paul, Minn.), polyurethanes, thermoplastic elastomers, copolymers comprising polyvinylidene difluoride ("PVDF"), pressure-sensitive adhesives, fluoroelastomers, polymers comprising silicone and acrylic moieties, or other suitable electroactive polymers. Polymers comprising silicone and acrylic moieties may include copolymers comprising silicone and acrylic moieties and polymer blends comprising a silicone elastomer and an acrylic elastomer. The electroactive polymer core 900 may also include combinations of some of the aforementioned materials. The electrodes 902 and 904 may be formed from a conductive material that is capable of elastically deforming over the range that electroactive polymer 900 is to be deformed. For example, the electrodes 902 and 904 may be formed from an elastomeric matrix having electrically conductive carbon particles dispersed therethrough.

With continued reference to FIG. 9A, when the strap structure 802a exhibits the length $L_O$, the voltage source 818 of the actuator system 808 is applying a selected voltage across the electrodes 902 and 904. For example, the user may select using the user interface 812 an installation setting that allows the user to don the orthotic apparatus 800 when the strap structures are in the elastically deformed, elongated state with an initial length $L_O$. The electroactive polymer material that comprises the electroactive polymer core 900 of the strap structure 802a increases in length response to an applied electric field, such as from an applied voltage. Referring to FIG. 9B, responsive to user input at the user interface 812, the magnitude of the applied voltage may be reduced so that the electroactive polymer core 900 contracts in length to a length $L_O$-$\Delta L$. Consequently, as the strap structure 802a contracts in length, the tension in the strap structure 802a gradually increases. Thus, by appropriately, reducing the applied voltage to the strap structures 802a and 802b, the tension in the strap structures 802a and 802b may be controlled. Accordingly, a controlled force may be applied to a user's knee to generate a valgus or varus moment to unload an affected compartment of the knee, as previously described.

During use, the tension in the strap structures 802a and 802b may change from the user's desired level. For example, the orthotic apparatus 800 may shift on the user's leg causing the tension to increase beyond the user's desired level. In such a scenario, the voltage across the first and second electrodes 902 and 904 changes as a result of the increased tension and strain of the strap structures 802a and 802b. The microprocessor 814 may be programmed to increase or decrease the magnitude of the voltage applied by the voltage source 818 to maintain a specific level set by the user at the user interface 812 responsive to voltage data from the voltage sensor 819.

The voltage sensor 819 may sense the change in voltage across the electroactive polymer core 900 of the strap structures 802a and 802b, and the microprocessor 814 may instruct the voltage source 818 to increase the voltage applied to the strap structures 802a and 802b to cause the strap structures 802a and 802b to increase in length responsive to the sensed voltage from the voltage sensor 819, thus, decreasing the tension therein.

Similar to the orthotic apparatus 100, in an embodiment, the memory 816 may store voltage data from the voltage sensor 819, and the control electronics 810 may include an output port for downloading the voltage data to, for example, a desktop computer for analysis by a medical professional. Additionally, as with the orthotic apparatus 100, the microprocessor 814 of the control electronics 810 may also be configured with different operational settings (e.g., a low-impact and a high-impact setting) that may be switched between the different operational settings responsive to user input at the user interface 812 or automatically, as previously described.

Figure 10A:
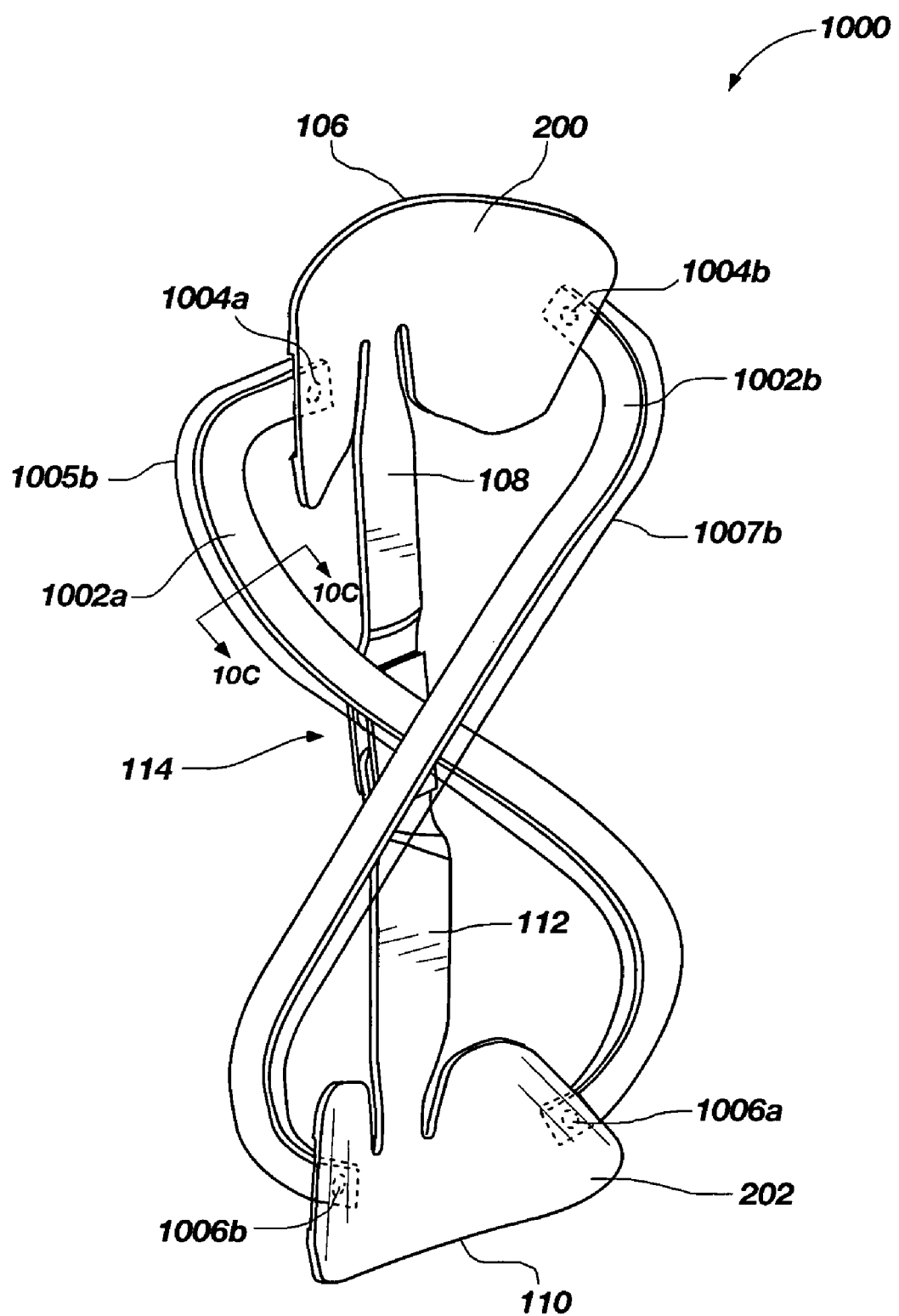
FIG. 10A is a rear perspective view of an orthotic apparatus including at least one strap structure having a shape memory alloy according to an embodiment.
Figure 10B:
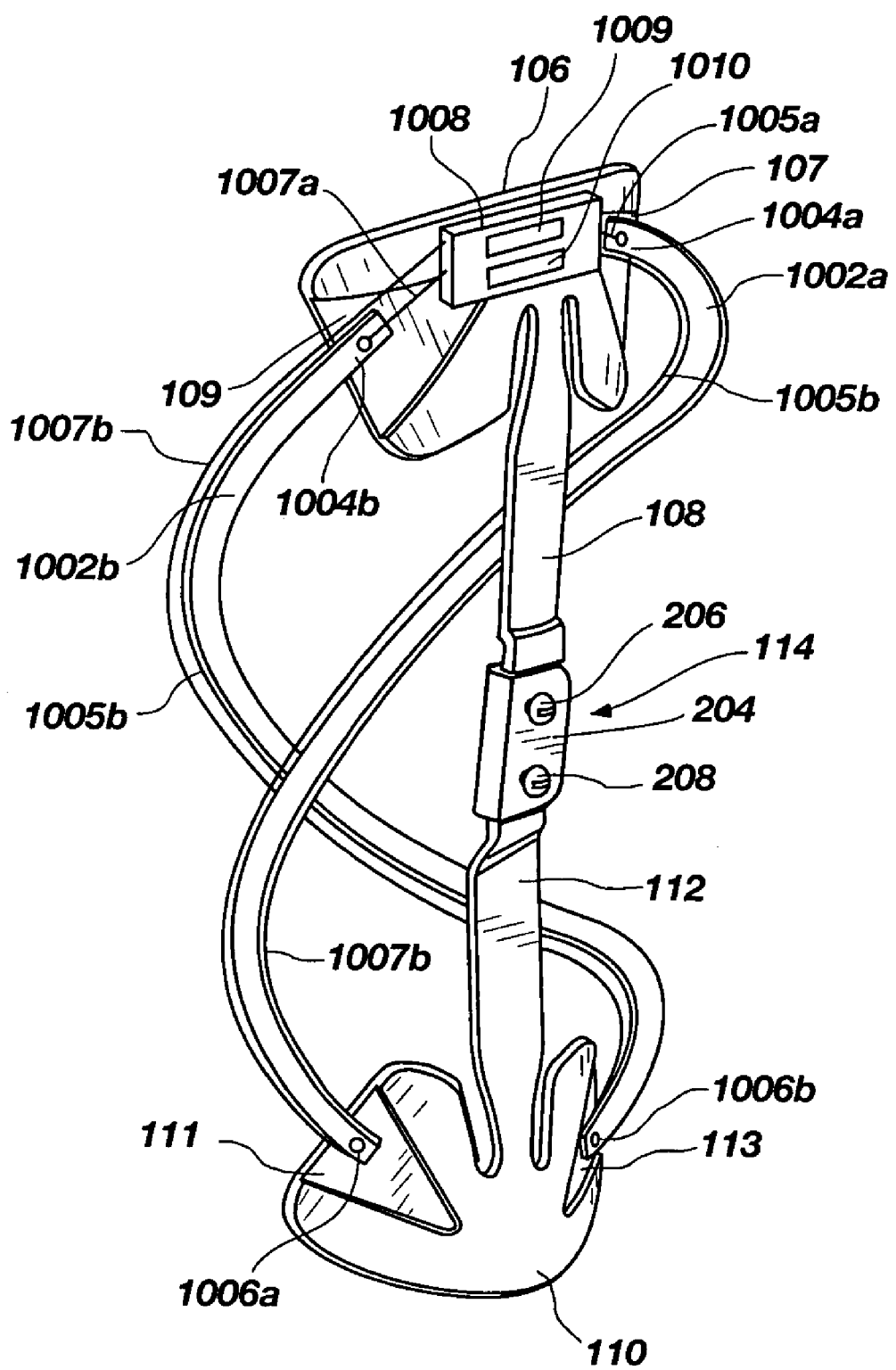
FIG. 10B is a front perspective view of the orthotic apparatus shown in FIG. 10A.

FIGS. 10A and 10B are rear and front perspective views, respectively, of an orthotic apparatus 1000 according to another embodiment. As will be discussed in more detail below, the orthotic apparatus 1000 utilizes strap structures 1002a and 1002b that each comprises wires formed from a shape memory alloy, with the length of the strap structures 1002a and 1002b controllable by heating the shape memory alloy. In the interest of brevity, the strap structures 1002a and 1002b are attached to the same frame structure 102 shown in the orthotic apparatus 100 of FIGS. 1A-1C and FIGS. 2A-2C. Therefore, components in both orthotic apparatuses 100 and 1000 that are identical to each other have been provided with the same reference numerals, and an explanation of their structure and function will not be repeated unless the components function differently in the two orthotic apparatuses 100 and 1000.

Still referring to FIGS. 10A and 10B, the strap structures 1002a and 1002b are attached to the frame structure 102. The strap structure 1002a has a proximal end 1004a and a distal end 1006a, with proximal end 1004a attached to the side 107 of the upper shell 106 of the frame structure 102 and the distal end 1006a attached to the side 111 of the lower shell 110 of the frame structure 102. The strap structure 1002b has a proximal end 1004b and a distal end 1006b, with proximal end 1004b attached to the side 109 of the upper shell 106 of the frame structure 102 and the distal end 1006b attached to the side 113 of the lower shell 110 of the frame structure 102. The strap structures 1002a and 1002b cross each other to form an "X" pattern similar to the manner in which the inflatable strap structures 116a and 116b shown in FIGS. 1A-1C cross each other.

Referring to FIG. 10B, the orthotic apparatus 1000 also includes an actuator system 1008 that may include similar functional components as the actuator system 808 shown in FIG. 8A. For example, the actuator system, 1008 may include a voltage source 1009 and control electronics 1010 operably coupled to the voltage source 1009. The control electronics 1010 may include a microprocessor, memory, and a user interface that are not illustrated. The voltage source 1009 may be electrically coupled to wires 1005a-b and 1007a-b. The wire 1005a may be electrically coupled to the proximal end 1004a of the strap structure 1002a and the wire 1005b is electrically coupled to the distal end 1006a of the strap structure 1002a. The wire 1007a may be electrically coupled to the proximal end 1004b of the strap structure 1002b and the wire 1007b is electrically coupled to the distal end 1006b of the strap structure 1002a. A current may be passed through each of the strap structures 1002a and 1002b by applying a voltage between wires 1005a and 1005b and a voltage between 1007a-b using the voltage source 1009.

Figure 10C:
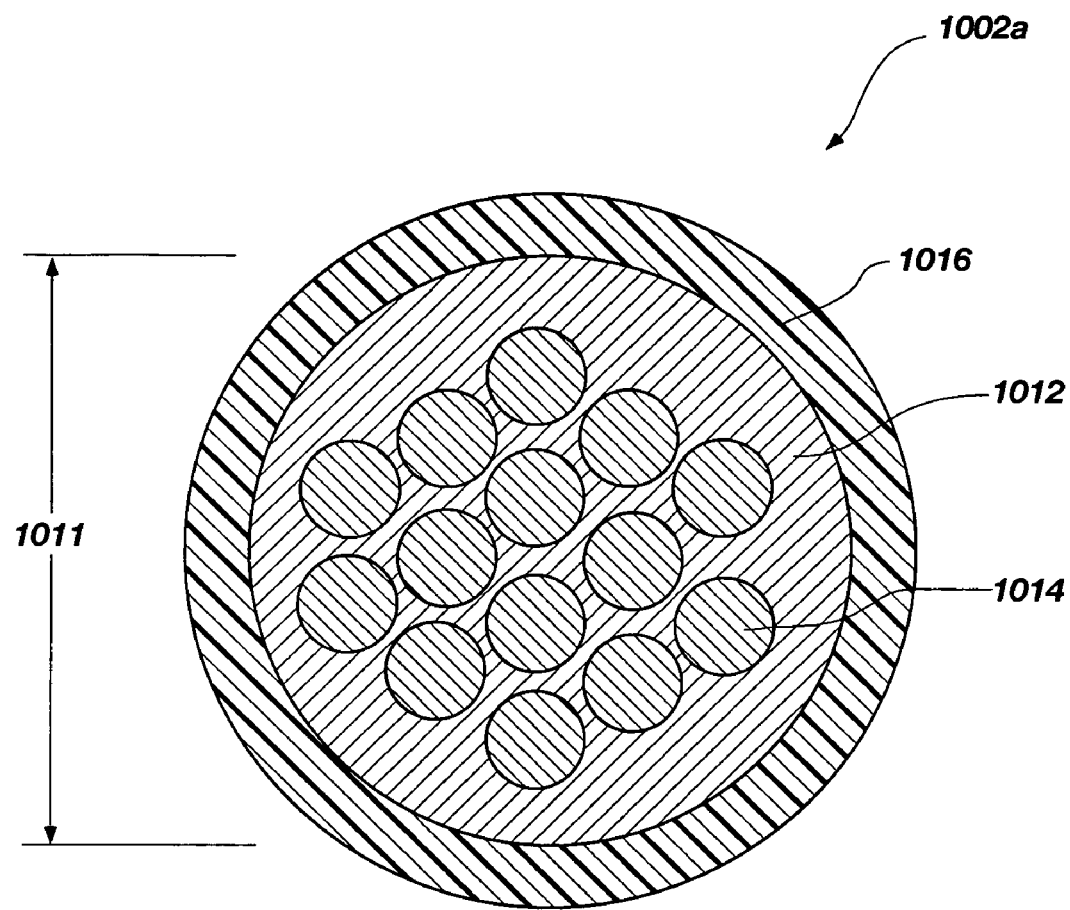
FIG. 10C is a cross-sectional view of one of the strap structures shown in FIG. 10A taken along line 10C-10C.

FIG. 10C is a cross-sectional view of the structure of the strap structures 1002a. Although FIG. 10C only shows a portion of the strap structure 1002a, the strap structure 1002b may have the same or similar structure as the illustrated strap structure 1002a and the strap structure 1002b may be operably coupled to the actuator system 1008 in the same or similar manner as the strap structure 1002a. The strap structure 1002a comprises a core 1011 including a matrix 1012 having a plurality of shape-memory-alloy wires 1014 embedded therein. For example, the matrix may be elastomer that, optionally, includes conductive particles (e.g., metallic or carbon particles) dispersed therethrough. The shape-memory-alloy wires 1014 may be formed from a number of different nickel-titanium alloys. Such nickel-titanium alloys are currently commercially available from Dynalloy, Inc. and sold under the trade name Flexinol®. For example, Flexinol HT® has a transition temperature of about 194° F., with an activation start temperature at about 190° F. and an activation finish temperature at about 208° F. A sheath 1016 may extend circumferentially about the core 1011 to thermally insulate the core 1011 from the user's leg. In an embodiment, the user may be thermally insulated from the core 1011 by cooling the exterior of the core 1011 using a coolant fluid using, for example, forced air or other heat transfer mechanism. In an embodiment, the strap structures 1002a and 1002b may comprise a bundle of shape-memory-alloy wires or a ribbon-like structure in which the shape memory alloy has a relatively high width to thickness ratio.

In operation, heating the strap structures 1002a and 1002b by, for example, passing a current therethrough using the voltage source 1009 causes the strap structures 1002a and 1002b to gradually and controllably contract in length as they are heated from the activation start temperature to the activation finish temperature. For example, the shape-memory-alloy wires 1014 may comprise Flexinol HT®, which is capable of contracting about 8 percent in length. Upon removal of the applied voltage, the strap structure 1002a elongates to the starting length. Thus, the strap structures 1002a and 1002b may be used to apply a controlled load to a user's knee to unload an affected compartment of the knee in a manner similar to the previously described orthotic apparatuses that employ an inflatable strap structure or a strap structure including an electroactive polymer.

Although various embodiments have been described in terms of orthotic apparatus for a joint (e.g., a knee), it is not intended that the subject matter described herein be limited to such an application. For example, the inflatable strap structures disclosed herein may be used in applications other than orthotic apparatuses for joints.

Referring to FIG. 11A, in an embodiment, one or more inflatable strap structures may be integrated in footwear as a replacement for conventional laces. FIG. 11A is a perspective view of a shoe 1100 according to an embodiment, which includes an inflatable strap structure 1102 and a pump 1104 operably coupled to the inflatable strap structure 1102. Referring to FIG. 11B, responsive to inflating the inflatable strap structure 1102 using the pump 1104, the inflatable strap structure 1102 contracts, as previously described, to secure the shoe 1100 on a user's foot. Footwear that requires a high tensioning force, such as snowboard boots, hiking boots, ski boots, biking shoes, ice skates, inline skates, to name a few, may employ an inflatable strap structure that is capable of controllably applying a load to secure the footwear on the user's foot. Further embodiments include equipment foot bindings, such as snowboard boot bindings, wake board bindings, water ski bindings, sail board bindings that utilize the inflatable strap structures to secure the user's foot in place. In some embodiments, a sensor (e.g., one or more accelerometers and/or pressure sensors) configured to sense a change in activity may provide feedback to control electronics operable to adjust the tension of the inflatable strap structure accordingly. In yet another embodiment, the inflatable strap structures may be used as a weight lifting belt and a compression sleeve.

While various aspects and embodiments have been disclosed herein, other aspects and embodiments are contemplated. The various aspects and embodiments disclosed herein are for purposes of illustration and are not intended to be limiting.

The invention claimed is:

1. An orthotic apparatus, comprising:
    an actuator system operable to provide input energy of a first type;
    a frame structure;
    at least one strap structure having a proximal end and a distal end defining a length, the at least one strap structure attached to the frame structure, the at least one strap structure operably coupled to the actuator system and configured to convert at least a portion of the input energy to energy of a second type, the energy of the second type being strain energy; and
    wherein the actuator system comprises control electronics that are programmed with a plurality of operational settings corresponding to different tension levels for the at least one strap structure, one of the plurality of operational settings corresponding to a first activity level and at least a second one of the plurality of operational settings corresponding to at least a second, different activity level.

2. The orthotic apparatus of claim 1 wherein:
    the actuator system comprises a pump in fluid communication with the at least one strap structure, the pump operable to pump fluid into the at least one strap structure; and
    the at least one strap structure comprises a plurality of inflatable chambers spaced along the length of the at least one strap structure, the at least one strap structure configured so that the length thereof decreases responsive to the inflatable chambers being inflated with the fluid.

3. The orthotic apparatus of claim 2 wherein the pump comprises one of:
    a manual pump; and
    an electromechanical pump.

4. The orthotic apparatus of claim 2 wherein the actuator system comprises:
    at least one relief valve;
    at least one sensor; and
    the control electronics are coupled to the pump, the at least one relief valve, and the at least one sensor, the control electronics operable to control the pump and the at least one relief valve responsive to sensing data from the at least one sensor in order to regulate pressure within the inflatable chambers of the at least one strap structure.

5. The orthotic apparatus of claim 4 wherein the control electronics are operable to maintain the pressure within the inflatable chambers at a substantially constant value.

6. The orthotic apparatus of claim 1 wherein:
    the actuator system comprises a voltage source; and
    the at least one strap structure comprises a core including an electroactive polymer disposed between and in electrical contact with first and second electrodes respectively electrically coupled to the voltage source, the length of the at least one strap structure increasing responsive to a voltage being applied by the voltage source between the first and the second electrodes.

7. The orthotic apparatus of claim 6 wherein the actuator system is operable to maintain a substantially constant tension in the at least one strap structure by controlling a magnitude of the voltage applied by the voltage source.

8. The orthotic apparatus of claim 6 wherein the electroactive polymer comprises one or more of the following electroactive materials:
a ferroelectric polymer;
a dielectric elastomer; and
an electrostrictive graft elastomer.

9. The orthotic apparatus of claim 1 wherein:
the frame structure comprises an upper shell having a first elongated support arm extending therefrom and a lower shell having a second elongated support arm extending therefrom, the first elongated support arm hingedly connected to the second elongated support arm; and
the at least one strap structure comprises a first strap structure and a second strap structure each of which is attached to the upper frame portion and the lower frame portion in a manner so that the first strap structure and the second strap structure cross each other.

10. The orthotic apparatus of claim 1 wherein the at least one strap structure is configured to elastically deform in a direction along the length thereof at least about 10 percent.

11. The orthotic apparatus of claim 10 wherein the at least one strap structure is configured to elastically deform in a direction along the length thereof about 10 percent to about 20 percent.

12. The orthotic apparatus of claim 1 wherein:
the at least one strap structure comprises one or more shape-memory-alloy wires; and
the actuator system is operable to controllably heat the one or more shape-memory-alloy wires to alter the length of the at least one strap structure.

13. The orthotic apparatus of claim 1 wherein the at least one strap structure comprises an inflatable strap structure that forms part of a larger, inflatable structure.

14. The orthotic apparatus of claim 1 wherein the actuator system comprises at least one sensor operable to sense changes in tension of the at least one strap structure and communicate the sensed changes to the control electronics, the control electronics being operable to automatically select one of the operational settings responsive to the sensed changes.

15. The orthotic apparatus of claim 1 wherein the control electronics comprise memory operable to store data corresponding to a tension of the at least one strap structure.

16. A method of using an orthotic apparatus, comprising:
programming a plurality of different operational settings into an actuator system operably coupled to at least one strap structure of the orthotic apparatus, the plurality of different operational settings correspond to different tension levels in the at least one strap structure, one of the plurality of operational settings corresponding to a first activity level and at least a second one of the plurality of operational settings corresponding to at least a second, different activity level;
donning the orthotic apparatus on a limb; and
changing a tension of the at least one strap structure responsive to inputting a first type of energy into the at least one strap structure in which at least a portion thereof is converted to strain energy.

17. The method of claim 16 wherein changing a tension of the at least one strap structure responsive to inputting a first type of energy into the at least one strap structure in which at least a portion thereof is converted to strain energy comprises inflating the at least one strap structure with a fluid to cause the at least one strap structure to contract in length.

18. The method of claim 16 wherein changing a tension of the at least one strap structure responsive to inputting a first type of energy into the at least one strap structure in which at least a portion thereof is converted to strain energy comprises decreasing a magnitude of a voltage applied to an electroactive polymer of the at least one strap structure to cause the at least one strap structure to contract in length.

19. The method of claim 16 wherein changing a tension of the at least one strap structure responsive to inputting a first type of energy into the at least one strap structure in which at least a portion thereof is converted to strain energy comprises heating one or more shape-memory-alloy wires of the at least one strap to cause the at least one strap structure to contract in length.

20. The method of claim 16, further comprising selecting an operational setting from among the plurality of different operational settings.

21. The method of claim 16, further comprising automatically selecting an operational setting from among the plurality of different operational settings responsive to sensing data corresponding to a tension of the at least one strap structure.

22. The method of claim 16 wherein changing a tension of the at least one strap structure responsive to inputting a first type of energy into the at least one strap structure in which at least a portion thereof is converted to strain energy comprises applying a voltage to an electroactive polymer of the at least one strap structure to cause the at least one strap structure to increase in length.

* * * * *